US006270993B1

(12) United States Patent
Shibuya et al.

(10) Patent No.: US 6,270,993 B1
(45) Date of Patent: Aug. 7, 2001

(54) VEGF-BINDING POLYPEPTIDE

(75) Inventors: Masabumi Shibuya, Saitama; Masaji Okamoto, Ibaraki; Mikio Niwa, Ibaraki; Tomoe Matsumoto, Ibaraki; Makoto Asano, Ibaraki; Tosiaki Segawa, Ibaraki, all of (JP)

(73) Assignee: Toa Gosei Co., Ltd., Tokyo (JP)

( * ) Notice: Subject to any disclaimer, the term of this patent is extended or adjusted under 35 U.S.C. 154(b) by 0 days.

(21) Appl. No.: 09/051,363

(22) PCT Filed: Oct. 7, 1996

(86) PCT No.: PCT/JP96/02906

§ 371 Date: Jul. 15, 1998

§ 102(e) Date: Jul. 15, 1998

(87) PCT Pub. No.: WO97/13787

PCT Pub. Date: Apr. 17, 1997

(30) Foreign Application Priority Data

Oct. 7, 1995 (JP) .................................... 7-286476
Jul. 23, 1996 (JP) .................................... 8-211892

(51) Int. Cl.$^7$ ............................ C07H 21/04; C12N 15/00
(52) U.S. Cl. ................. 435/69.1; 435/325; 435/252.3; 435/254.11; 435/320.1; 536/23.1; 536/23.4; 536/23.5
(58) Field of Search .......................... 530/350; 435/320.1, 435/252.3, 69.1, 325, 254.11; 536/23.4, 23.5, 23.1

(56) References Cited

U.S. PATENT DOCUMENTS 6,011,003 * 1/2000 Charnock-Jones et al. ............. 514/2
6,100,071 * 8/2000 Smyth et al. ........................ 435/69.7

FOREIGN PATENT DOCUMENTS

WO 94/10202  5/1994 (WO).
WO 94/21679  9/1994 (WO).
WO 95/33050  7/1995 (WO).
   95/33050 * 12/1995 (WO).

OTHER PUBLICATIONS

Aiello et al., "Suppression of retinal neovascularization in vivo by inhibition . . . ", Proc. Natl. Acad. Sci. USA 92:10457–10461, 1995.
Boocock et al., "Expression of Vascular Endothelial Growth Factor and Its Receptors . . . ", Journal of the National Cancer Institute 87:506–516, 1995.
Gengrinovitch et al., "Platelet Factor—4 Inhibits the Mitogenic Activity of VEGF$_{121}$ and . . . ", J. Biol. Chem. 270:15059–15065, 1995.
Kendall et al., "Inhibition of vascular endothelial cell growth factor activity by an . . . ", Proc. Natl. Acad. Sci. USA 90:10705–10709, 1993.
Kendall et al., "Specificity of vascular endothelial cell growth factor receptor ligand . . . ", Biochemical and Biophysical Research Communications 201:326–330, 1994.
Wang et al., "Identification of the Ligand–Binding Regions in the Macrophage Colony . . . ",Molecular and Cellular Biology, 13:5348–5359, 1993.
Hollenbaugh et al., Current Protocols in Immunology, Unit 10,19, 1992. "Construction of Immunoglobulin Fusion Proteins".*
M. Shibuya et al., "Nucleotide sequence and expression of a novel human receptor–type tyrosine kinase gene (*flt*) closely related to the *fms* family", Oncogene 5:519–524, 1990.*

* cited by examiner

Primary Examiner—Lorraine Spector
(74) Attorney, Agent, or Firm—Fish & Richardson P.C.

(57) ABSTRACT

An object of the present invention is to provide a low molecular weight VEGF inhibitor that can be utilized to treat diseases accompanying neovascularization, such as solid tumors. It was found that a polypeptide containing immunoglobulin-like domain 1 and immunoglobulin-like domain 2 but neither immunoglobulin-like main 6 nor immunoglobulin-like domain 7 of the extracellular domain of the VEGF receptor FLT possess VEGF inhibitory activity.

11 Claims, 14 Drawing Sheets

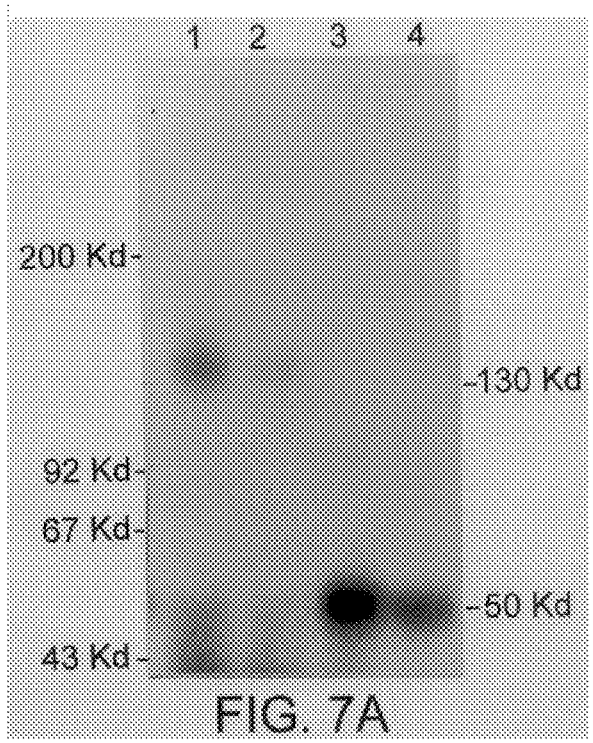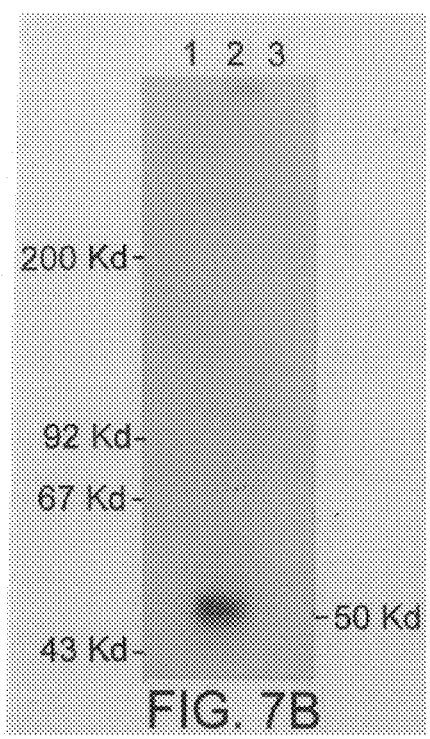

FIG. 9B

```
                           SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
           (A) LENGTH: 2523 base pairs
           (B) TYPE: nucleic acid
           (C) STRANDEDNESS: double
           (D) TOPOLOGY: linear (ii) MOLECULE TYPE: cDNA (vi) ORIGINAL SOURCE:
           (A) ORGANISM: Homo sapiens
           (G) CELL TYPE: placental tissue (ix) FEATURE:
           (A) NAME/KEY: Coding Sequence
           (B) LOCATION: 250...2523

(xi) SEQUENCE DESCRIPTION: SEQ ID NO:1:

GCGGACACTC CTCTCGGCTC CTCCCCGGCA GCGGCGGCGG CTCGGAGCGG GCTCCGGGGC          60

TCGGGTGCAG CGGCCAGCGG GCCTGGCGGC GAGGATTACC CGGGGAAGTG GTTGTCTCCT         120

GGCTGGAGCC GCGAGACGGG CGCTCAGGGC GCGGGGCCGG CGGCGGCGAA CGAGAGGACG         180

GACTCTGGCG GCCGGGTCGT TGGCCGGGGG AGCGCGGGCA CCGGGCGAGC AGGCCGCGTC         240

GCGCTCACC ATG GTC AGC TAC TGG GAC ACC GGG GTC CTG CTG TGC GCG CTG         291
          Met Val Ser Tyr Trp Asp Thr Gly Val Leu Leu Cys Ala Leu
            1               5                  10

CTC AGC TGT CTG CTT CTC ACA GGA TCT AGT TCA GGT TCA AAA TTA AAA           339
Leu Ser Cys Leu Leu Leu Thr Gly Ser Ser Ser Gly Ser Lys Leu Lys
 15                  20                  25                  30

GAT CCT GAA CTG AGT TTA AAA GGC ACC CAG CAC ATC ATG CAA GCA GGC           387
Asp Pro Glu Leu Ser Leu Lys Gly Thr Gln His Ile Met Gln Ala Gly
                35                  40                  45
```

```
CAG ACA CTG CAT CTC CAA TGC AGG GGG GAA GCA GCC CAT AAA TGG TCT        435
Gln Thr Leu His Leu Gln Cys Arg Gly Glu Ala Ala His Lys Trp Ser
        50                      55                      60

TTG CCT GAA ATG GTG AGT AAG GAA AGC GAA AGG CTG AGC ATA ACT AAA        483
Leu Pro Glu Met Val Ser Lys Glu Ser Glu Arg Leu Ser Ile Thr Lys
        65                      70                      75

TCT GCC TGT GGA AGA AAT GGC AAA CAA TTC TGC AGT ACT TTA ACC TTG        531
Ser Ala Cys Gly Arg Asn Gly Lys Gln Phe Cys Ser Thr Leu Thr Leu
        80                      85                      90

AAC ACA GCT CAA GCA AAC CAC ACT GGC TTC TAC AGC TGC AAA TAT CTA        579
Asn Thr Ala Gln Ala Asn His Thr Gly Phe Tyr Ser Cys Lys Tyr Leu
 95                     100                     105                 110

GCT GTA CCT ACT TCA AAG AAG AAG GAA ACA GAA TCT GCA ATC TAT ATA        627
Ala Val Pro Thr Ser Lys Lys Lys Glu Thr Glu Ser Ala Ile Tyr Ile
                115                     120                     125

TTT ATT AGT GAT ACA GGT AGA CCT TTC GTA GAG ATG TAC AGT GAA ATC        675
Phe Ile Ser Asp Thr Gly Arg Pro Phe Val Glu Met Tyr Ser Glu Ile
                130                     135                     140

CCC GAA ATT ATA CAC ATG ACT GAA GGA AGG GAG CTC GTC ATT CCC TGC        723
Pro Glu Ile Ile His Met Thr Glu Gly Arg Glu Leu Val Ile Pro Cys
        145                     150                     155

CGG GTT ACG TCA CCT AAC ATC ACT GTT ACT TTA AAA AAG TTT CCA CTT        771
Arg Val Thr Ser Pro Asn Ile Thr Val Thr Leu Lys Lys Phe Pro Leu
        160                     165                     170

GAC ACT TTG ATC CCT GAT GGA AAA CGC ATA ATC TGG GAC AGT AGA AAG        819
Asp Thr Leu Ile Pro Asp Gly Lys Arg Ile Ile Trp Asp Ser Arg Lys
175                     180                     185                 190

GGC TTC ATC ATA TCA AAT GCA ACG TAC AAA GAA ATA GGG CTT CTG ACC        867
Gly Phe Ile Ile Ser Asn Ala Thr Tyr Lys Glu Ile Gly Leu Leu Thr
                195                     200                     205

TGT GAA GCA ACA GTC AAT GGG CAT TTG TAT AAG ACA AAC TAT CTC ACA        915
Cys Glu Ala Thr Val Asn Gly His Leu Tyr Lys Thr Asn Tyr Leu Thr
                210                     215                     220

CAT CGA CAA ACC AAT ACA ATC ATA GAT GTC CAA ATA AGC ACA CCA CGC        963
His Arg Gln Thr Asn Thr Ile Ile Asp Val Gln Ile Ser Thr Pro Arg
                225                     230                     235

CCA GTC AAA TTA CTT AGA GGC CAT ACT CTT GTC CTC AAT TGT ACT GCT       1011
Pro Val Lys Leu Leu Arg Gly His Thr Leu Val Leu Asn Cys Thr Ala
        240                     245                     250

ACC ACT CCC TTG AAC ACG AGA GTT CAA ATG ACC TGG AGT TAC CCT GAT       1059
Thr Thr Pro Leu Asn Thr Arg Val Gln Met Thr Trp Ser Tyr Pro Asp
255                     260                     265                 270

GAA AAA AAT AAG AGA GCT TCC GTA AGG CGA CGA ATT GAC CAA AGC AAT       1107
Glu Lys Asn Lys Arg Ala Ser Val Arg Arg Arg Ile Asp Gln Ser Asn
                275                     280                     285

TCC CAT GCC AAC ATA TTC TAC AGT GTT CTT ACT ATT GAC AAA ATG CAG       1155
Ser His Ala Asn Ile Phe Tyr Ser Val Leu Thr Ile Asp Lys Met Gln
                290                     295                     300

AAC AAA GAC AAA GGA CTT TAT ACT TGT CGT GTA AGG AGT GGA CCA TCA       1203
Asn Lys Asp Lys Gly Leu Tyr Thr Cys Arg Val Arg Ser Gly Pro Ser
                305                     310                     315

TTC AAA TCT GTT AAC ACC TCA GTG CAT ATA TAT GAT AAA GCA TTC ATC       1251
Phe Lys Ser Val Asn Thr Ser Val His Ile Tyr Asp Lys Ala Phe Ile
        320                     325                     330

ACT GTG AAA CAT CGA AAA CAG CAG GTG CTT GAA ACC GTA GCT GGC AAG       1299
Thr Val Lys His Arg Lys Gln Gln Val Leu Glu Thr Val Ala Gly Lys
335                     340                     345                 350

CGG TCT TAC CGG CTC TCT ATG AAA GTG AAG GCA TTT CCC TCG CCG GAA       1347
Arg Ser Tyr Arg Leu Ser Met Lys Val Lys Ala Phe Pro Ser Pro Glu
```

```
                         355                     360                         365
GTT GTA TGG TTA AAA GAT GGG TTA CCT GCG ACT GAG AAA TCT GCT CGC      1395
Val Val Trp Leu Lys Asp Gly Leu Pro Ala Thr Glu Lys Ser Ala Arg
                370                     375                 380

TAT TTG ACT CGT GGC TAC TCG TTA ATT ATC AAG GAC GTA ACT GAA GAG      1443
Tyr Leu Thr Arg Gly Tyr Ser Leu Ile Ile Lys Asp Val Thr Glu Glu
                385                     390                 395

GAT GCA GGG AAT TAT ACA ATC TTG CTG AGC ATA AAA CAG TCA AAT GTG      1491
Asp Ala Gly Asn Tyr Thr Ile Leu Leu Ser Ile Lys Gln Ser Asn Val
            400                     405                 410

TTT AAA AAC CTC ACT GCC ACT CTA ATT GTC AAT GTG AAA CCC CAG ATT      1539
Phe Lys Asn Leu Thr Ala Thr Leu Ile Val Asn Val Lys Pro Gln Ile
415                     420                 425                 430

TAC GAA AAG GCC GTG TCA TCG TTT CCA GAC CCG GCT CTC TAC CCA CTG      1587
Tyr Glu Lys Ala Val Ser Ser Phe Pro Asp Pro Ala Leu Tyr Pro Leu
                    435                 440                 445

GGC AGC AGA CAA ATC CTG ACT TGT ACC GCA TAT GGT ATC CCT CAA CCT      1635
Gly Ser Arg Gln Ile Leu Thr Cys Thr Ala Tyr Gly Ile Pro Gln Pro
                450                     455                 460

ACA ATC AAG TGG TTC TGG CAC CCC TGT AAC CAT AAT CAT TCC GAA GCA      1683
Thr Ile Lys Trp Phe Trp His Pro Cys Asn His Asn His Ser Glu Ala
                465                     470                 475

AGG TGT GAC TTT TGT TCC AAT AAT GAA GAG TCC TTT ATC CTG GAT GCT      1731
Arg Cys Asp Phe Cys Ser Asn Asn Glu Glu Ser Phe Ile Leu Asp Ala
        480                     485                 490

GAC AGC AAC ATG GGA AAC AGA ATT GAG AGC ATC ACT CAG CGC ATG GCA      1779
Asp Ser Asn Met Gly Asn Arg Ile Glu Ser Ile Thr Gln Arg Met Ala
495                     500                 505                 510

ATA ATA GAA GGA AAG AAT AAG ATG GCT AGC ACC TTG GTT GTG GCT GAC      1827
Ile Ile Glu Gly Lys Asn Lys Met Ala Ser Thr Leu Val Val Ala Asp
                    515                 520                 525

TCT AGA ATT TCT GGA ATC TAC ATT TGC ATA GCT TCC AAT AAA GTT GGG      1875
Ser Arg Ile Ser Gly Ile Tyr Ile Cys Ile Ala Ser Asn Lys Val Gly
                530                     535                 540

ACT GTG GGA AGA AAC ATA AGC TTT TAT ATC ACA GAT GTG CCA AAT GGG      1923
Thr Val Gly Arg Asn Ile Ser Phe Tyr Ile Thr Asp Val Pro Asn Gly
            545                     550                 555

TTT CAT GTT AAC TTG GAA AAA ATG CCG ACG GAA GGA GAG GAC CTG AAA      1971
Phe His Val Asn Leu Glu Lys Met Pro Thr Glu Gly Glu Asp Leu Lys
            560                     565                 570

CTG TCT TGC ACA GTT AAC AAG TTC TTA TAC AGA GAC GTT ACT TGG ATT      2019
Leu Ser Cys Thr Val Asn Lys Phe Leu Tyr Arg Asp Val Thr Trp Ile
575                     580                 585                 590

TTA CTG CGG ACA GTT AAT AAC AGA ACA ATG CAC TAC AGT ATT AGC AAG      2067
Leu Leu Arg Thr Val Asn Asn Arg Thr Met His Tyr Ser Ile Ser Lys
                    595                 600                 605

CAA AAA ATG GCC ATC ACT AAG GAG CAC TCC ATC ACT CTT AAT CTT ACC      2115
Gln Lys Met Ala Ile Thr Lys Glu His Ser Ile Thr Leu Asn Leu Thr
                610                     615                 620

ATC ATG AAT GTT TCC CTG CAA GAT TCA GGC ACC TAT GCC TGC AGA GCC      2163
Ile Met Asn Val Ser Leu Gln Asp Ser Gly Thr Tyr Ala Cys Arg Ala
            625                     630                 635

AGG AAT GTA TAC ACA GGG GAA GAA ATC CTC CAG AAG AAA GAA ATT ACA      2211
Arg Asn Val Tyr Thr Gly Glu Glu Ile Leu Gln Lys Lys Glu Ile Thr
            640                     645                 650

ATC AGA GAT CAG GAA GCA CCA TAC CTC CTG CGA AAC CTC AGT GAT CAC      2259
Ile Arg Asp Gln Glu Ala Pro Tyr Leu Leu Arg Asn Leu Ser Asp His
655                     660                 665                 670

ACA GTG GCC ATC AGC AGT TCC ACC ACT TTA GAC TGT CAT GCT AAT GGT      2307
```

```
Thr Val Ala Ile Ser Ser Ser Thr Thr Leu Asp Cys His Ala Asn Gly
            675                 680                 685
GTC CCC GAG CCT CAG ATC ACT TGG TTT AAA AAC AAC CAC AAA ATA CAA      2355
Val Pro Glu Pro Gln Ile Thr Trp Phe Lys Asn Asn His Lys Ile Gln
            690                 695                 700
CAA GAG CCT GGA ATT ATT TTA GGA CCA GGA AGC AGC ACG CTG TTT ATT      2403
Gln Glu Pro Gly Ile Ile Leu Gly Pro Gly Ser Ser Thr Leu Phe Ile
            705                 710                 715
GAA AGA GTC ACA GAA GAG GAT GAA GGT GTC TAT CAC TGC AAA GCC ACC      2451
Glu Arg Val Thr Glu Glu Asp Glu Gly Val Tyr His Cys Lys Ala Thr
            720                 725                 730
AAC CAG AAG GGC TCT GTG GAA AGT TCA GCA TAC CTC ACT GTT CAA GGA      2499
Asn Gln Lys Gly Ser Val Glu Ser Ser Ala Tyr Leu Thr Val Gln Gly
735                 740                 745                 750
ACC TCG GAC AAG TCT AAT CTG GAG                                      2523
Thr Ser Asp Lys Ser Asn Leu Glu
            755
```

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:2:

CGTCGCGCTC ACCATGGTCA G                                              21

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:3:

TTATTCGTAA ATCTGGGGTT TCAC                                           24

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:4:

TATTAATGAT CTAGATGAC                                                 19

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

TCGAGTCATT CTAGATCATT AA                                               22

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

AGCTTTTAAT GATCTAGAAT GAC                                              23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

TCGAGTCATT CTAGATCATT AAA                                              23

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:8:

CTCGGATCCG GATCTAGTTC AGGTTCAAAA                                       30

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:9:

CTCGAATTCA CTCCAGATTA GACTTGTCCG A                                     31

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:10:

TTTCTCGGAT CCTATAAATA TGGTCAGCTA CTGGGACACC                             40

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:11:

```
GTGGTGGTGG TGGTGGTGAC GCTCCAGATT AGACTTGTCC GA                42
```

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:12:

```
CACCACCACC ACCACCACTA ACTAGAGCTC GCTGATC                      37
```

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:13:

```
TTCTCGAATT CTCCCCAGCA TGCCTGC                                 27
```

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:14:

```
TCTTGTGACA AAACTCACAC ATGC                                    24
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:15:

```
CGGAGACAGG GAGAGGCTCT TCTG                                    24
```

(2) INFORMATION FOR SEQ ID NO:16:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:16:

GAGCCCAAAT CTTGTGACAA AA         22

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:17:

TTCTCGGATC CTTATTTACC CGGAGACAGG GA         32

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:18:

TAACCTGGCG ATAACGAGGC GCAAATAATG AAAAAG         36

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:19:

CTGAACTAGA TTTCGGAGCG GCCTGCGCTA         30

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:20:

TTCTCGAATT CCCTGTGGAG TTATATATGA GC         32

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:21:

GCCTCGTTAT CGCCAGGTTA GCGTCGAGGA                                                30

(2) INFORMATION FOR SEQ ID NO:22:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: synthetic DNA (xi) SEQUENCE DESCRIPTION: SEQ ID NO:22:

CGCTCCGAAA TCTAGTTCAG GTTCAAAATT                                                30

(2) INFORMATION FOR SEQ ID NO:23:

(i) SEQUENCE CHARACTERISTICS:
              (A) LENGTH: 42 base pairs
              (B) TYPE: nucleic acid
              (C) STRANDEDNESS: single
              (D) TOPOLOGY: linear (ii) MOLECULE TYPE: synthetic DNA (xi) SEQUENCE DESCRIPTION: SEQ ID NO:23:

TTTGTCACAA GATTTGGGCT CTGTGCTTAT TTGGACATCT AT                                  42

(2) INFORMATION FOR SEQ ID NO:24:

(i) SEQUENCE CHARACTERISTICS:
              (A) LENGTH: 758 amino acids
              (B) TYPE: amino acid
              (D) TOPOLOGY: linear (ii) MOLECULE TYPE: protein (v) FRAGMENT TYPE: internal (xi) SEQUENCE DESCRIPTION: SEQ ID NO:24:

Met Val Ser Tyr Trp Asp Thr Gly Val Leu Leu Cys Ala Leu Leu Ser
  1               5                  10                  15

Cys Leu Leu Thr Gly Ser Ser Ser Gly Ser Lys Leu Lys Asp Pro
                 20                  25                  30

Glu Leu Ser Leu Lys Gly Thr Gln His Ile Met Gln Ala Gly Gln Thr
             35                  40                  45

Leu His Leu Gln Cys Arg Gly Glu Ala Ala His Lys Trp Ser Leu Pro
         50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val

```
                145                 150                 155                 160
Thr Ser Pro Asn Ile Thr Val Thr Leu Lys Lys Phe Pro Leu Asp Thr
                    165                 170                 175
Leu Ile Pro Asp Gly Lys Arg Ile Ile Trp Asp Ser Arg Lys Gly Phe
                180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
        210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
        530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
```

-continued

```
Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
        690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu
            755
```

VEGF-BINDING POLYPEPTIDE

TECHNICAL FIELD

The present invention relates to polypeptides which are useful as neovascularization inhibitors, and a method of producing them.

BACKGROUND ART

It is known that pathological neovascularization is closely related to the symptoms or causes of certain diseases. Solid tumors are representative of such diseases. For the growth of tumor tissue beyond the diameter of 1 to 2 mm, newly formed blood vessels need to extend from the existing blood vessels to reach the tumor tissue (J. Folkman, J. Natl. Cancer Inst., 82:4 (1990)). When the blood vessel reaches the tumor tissue, its growth is explosively accelerated. Diabetic retinopathy is accompanied by pathological neovascularization of the retina, which often leads to the loss of eyesight. Moreover, pathological neovascularization is also seen in such diseases as chronic rheumatoid arthritis, psoriasis, hemangioma, scleroderma, and neovascular glaucomas, and it is considered to be one of the main symptoms (J. Folkman and N. Engle, J. Med., 320:1211 (1989)). Therefore, it may be possible to use substances that inhibit neovascularization for the treatment of tumors and other diseases mentioned above.

Vascular endothelial cells are the cells that constitute the innermost layer of the blood vessel. Neovascularization occurs when vascular endothelial cells proliferate upon stimulation by growth factors, physiologically active substances, or mechanical damages. Known growth factors that can directly or indirectly stimulate the proliferation of vascular endothelial cells include bFGF (basic Fibroblast Growth Factor), aFGF (acidic Fibroblast Growth Factor), VEGF (Vascular Endothelial cell Growth Factor), PD-ECGF (Platelet-Derived Endothelial Cell Growth Factor), TNF-α (Tumor Necrosis Factor-α), PDGF (Platelet-Derived Growth Factor), EGF (Epidermal Growth Factor), TGF-α (Transforming Growth Factor-α), and HGF (Hepatocyte Growth Factor) (L. Diaz-Flores et al., Histol. Histopath., 9:807 (1994)). Particularly, VEGF can be distinguished from the other growth factors by the fact that its action is very specific to vascular endothelial cells. In other words, the VEGF receptor is found in very few cells other than vascular endothelial cells.

VEGF is a glycoprotein whose molecular weight is 40,000–45,000, and exists as a dimer (P. W. Leung et al., Science, 246:1306 (1989), P. J. Keck et al., Science, 246:1319 (1989)). VEGF acts, by binding to the VEGF receptor, to promote cell proliferation and enhance membrane permeability.

The following reports suggest the involvement of VEGF in tumor. Many tumor cells secrete VEGF (S. Kondo et al., Biochem. Biophys. Res. Commun., 194:1234 (1993)). When tumor tissue sections are stained with an anti-VEGF antibody, the tumor tissue is strongly stained as well as the newly formed blood vessels surrounding it (H. F. Dvorak et al., J. Exp. Med. 174:1275 (1991), L. F. Brown et al., Cancer Res., 53:4727 (1993)). Growth of a transplanted tumor is suppressed in mice in which one of the VEGF receptors is genetically inactivated (B. Millauer et al., Nature, 367:576 (1994)). Anti-VEGF neutralizing antibodies exhibit antitumor activities in tumor-bearing mice (K. J. Kim et al., Nature, 362:841 (1993), S. Kondo et al., Biochem. Biophys. Res. Commun., 194:1234 (1993)). From these facts, it is considered that VEGF secreted by tumor cells plays a major role in neoplastic neovascularization.

In humans there are two known VEGF receptors, FLT (M. Shibuya et al., Oncogene, 5:519 (1990)) and KDR (B. I. Terman et al., Biochem. Biophys. Res. Commun., 187:1579 (1992)). The extracellular domain of FLT (also known in the art as FLT-1) has seven immunoglobulin-like domains as shown in FIG. 1 (C. DeVries et al., Science, 255:989 (1992)). Regarding FLT, a cDNA of a soluble-type receptor has been cloned (R. L. Kendal and K. A. Thomas, Proc. Natl. Acad. Sci. U.S.A., 90:10705 (1993)). The polypeptide encoded by this cDNA corresponds to the first through sixth immunoglobulin-like domains of the seven immunoglobulin-like domains of the FLT extracellular domain, and it inhibited the VEGF activities by binding to VEGF with an affinity comparable to that of the full-length FLT. Regarding KDR, it is also known that the genetically engineered first through sixth immunoglobulin-like domains of the extracellular domain bind to VEGF (R. L. Kendal et al., Biochem. Biophys. Res. Commun., 201:326(1994)).

DISCLOSURE OF THE INVENTION

Since the mouse anti-VEGF neutralizing antibodies exhibit antitumor activity, they are expected to be useful as anti-cancer agents. However, when a mouse antibody is administered to humans, human antibodies against the mouse antibody may be produced, which could lead to neutralization of the mouse antibody or might cause anaphylactic shock. In order to avoid these undesirable effects, it is necessary to modify the amino acid sequence of the mouse antibody to be closer to that of the human antibody through chimeralization (S. L. Morrison et al., Proc. Natl. Acad. Sci. U.S.A., 81:6851 (1989)) or humanization without reducing the neutralizing activity of the mouse antibody. Since this method requires advanced techniques and knowledge, experience, and labor, the results depend on individual cases and are not always successful. Furthermore, 100%-humanized antibodies cannot be obtained by these methods. Another method utilizes transgenic mice that produce human antibodies for immunization (S. Wagner et al., Nucleic Acid Res., 22:1389 (1994)), but here again highly specialized techniques are required.

As described above, since the extracellular domain of the VEGF receptor specifically binds to VEGF with high affinity, thereby inhibiting the VEGF activity, it can be considered useful as an inhibitor against neovascularization. Moreover, the possibility of antibody production in a human recipient is expected to be low because it is a polypeptide of human origin. However, it has been reported that when a polypeptide that does not naturally exist much in the human body is administered, it is metabolized very rapidly. For example, the plasma half-life of soluble CD4, which is a receptor for HIV, is 15 minutes (D. J. Capon et al., Nature, 337:525 (1989)), and that of interferon γ is 30 minutes (I. Rutenfranz and H. Kirchner, J. Interferon Res., 8:573 (1988)).

As a method for prolonging the plasma half-life, it is known to utilize a fusion polypeptide genetically engineered by combining the polypeptide of interest with a molecule having a long plasma half-life, such as an antibody molecule. In the case of CD4, the plasma half-life was increased from 15 min to 48 hr when it was chimerilized with the Fc domain of IgG1 (D. J. Capon et al., Nature, 337:525 (1989)). Such a fusion polypeptide with the Fc domain of an antibody is also expected to provide an effect to induce the effector functions that the antibody possesses, i.e., complement-dependent cytotoxicity (D. B. Amos et al., Transplantation, 7:220 (1969)) and antibody-dependent cytotoxicity (A. Y. Liu et al., Proc. Natl. Acad. Sci. U.S.A., 84:3439 (1987)).

Furthermore, it is expected to drastically improve the apparent affinity when the fusion polypeptide binds to a ligand on a solid phase, such as the surface of a membrane or the extracellular matrix, since the dimerization via the Fc domain enables each molecule to bind to the ligand at two sites.

When a fusion polypeptide constructed with an antibody is utilized, it is desirable to select a polypeptide with a low molecular weight as a starting material because the molecular weight increases through the fusion. This is because, if a high molecular weight polypeptide is used, the molecular weight of the corresponding DNA is also high, which is to be handled by gene manipulation upon production of the recombinant host that produces the fusion polypeptide. In general, the larger the molecular weight of the DNA to be introduced, the less efficient the transfection of the host becomes, thereby reducing the productivity of the recombinant host. Also in general, the larger the molecular weight of the recombinant polypeptide to be produced, the smaller the amount of product tends to be. Moreover, for the treatment of solid tumors, large molecular weight polypeptides have been reported to show a poor infiltration capability into the diseased area (D. M. Lane et al., Br. J. Cancer, 70:521 (1994)).

The present inventors have made earnest efforts in discovering small molecular weight polypeptides which can inhibit neovascularization by specifically inhibiting VEGF, and particularly those which are contained in the extracellular domain of the VEGF receptor. As a result, it has been found that polypeptides containing immunoglobulin-like domain 1 and immunoglobulin-like domain 2 of the extracellular domain of FLT can inhibit the VEGF activities by specifically binding to VEGF with high affinity. The term "polypeptides" used herein means molecules constituted by amino acids that are covalently bound to each other via peptide bonds, and the lengths of the molecules are not limited.

The polypeptides of the present invention include, in addition to the ones consisting of immunoglobulin-like domain 1 and immunoglobulin-like domain 2 of the extracellular domain of FLT, those which contain other domains.

Immunoglobulin-like domain 1: 1–110
Immunoglobulin-like domain 2: 111–208
Immunoglobulin-like domain 3: 209–311
Immunoglobulin-like domain 4: 312–407
Immunoglobulin-like domain 5: 408–535
Immunoglobulin-like domain 6: 536–640
Immunoglobulin-like domain 7: 641–736

Furthermore, the present invention includes the polypeptides constructed by fusing the above extracellular domain of FLT with another protein (such as the Fc domain of immunoglobulins).

These peptides can be produced by the following procedures. A total RNA is extracted by the acid phenol method (P. Chomzynski and N. Sacchi, Anal. Biochem., 162:156 (1987)) from the cultured human vascular endothelial cells, such as human umbilical chord-derived vascular endothelial cells (commercially available from Iwaki Glass, Morinaga Dairy Products, or Kurabo), and purified into a poly $A^+$ RNA using an oligo dT cellulose. A single-stranded or double-stranded cDNA is synthesized using this RNA as a template, reverse transcriptase, and the oligo dT (12–16) primer. The poly $A^+$ RNA and the cDNA can be prepared in accordance with "Molecular Cloning" (by J. Sambrook et al., Cold Spring Harbor Laboratory Press, 1989). Alternatively, the commercially available poly $A^+$ RNA preparation reagents (oligotex-dT30, Takara) or cDNA synthesis kit (Pharmacia Biosystem) can be used. If an flt cDNA has been already cloned from a cDNA library, the DNA corresponding to the region to be expressed can be isolated by digestion with appropriate restriction enzymes and introduced directly into an expression vector.

Next, a desired part of the DNA can be amplified by PCR using the cDNA obtained above as the template (refer to "PCR protocols", Academic Press Inc., 1990). For instance, the following primers may be used. The primer DNA can be synthesized with a DNA synthesizer (Applied Biosystems, Japan Millipore Ltd., etc.) or custom-made (Sawadee Technology). For example, in the case of obtaining a cDNA encoding immunoglobulin-like domains 1 through 4, the following primers can be used:

```
Upstream primer:
    5'-N (3-5) X (6) CGTCGCGCTCACCATGGTCAG-3'    (SEQ ID NO:2)

downstream primer:
    5'-N (3-5) Y (6) TTATTCGTAAATCTGGGGTTTCAC-3'  (SEQ ID NO:3).
```

For example, they include the polypeptides containing immunoglobulin-like domains 1 through 4 and those containing immunoglobulin-like domains 1 through 5. On the other hand, the polypeptides containing immunoglobulin-like domains 1 through 6 and those containing immunoglobulin-like domains 1 through 7 are excluded from the polypeptides of the present invention, because their molecular weights are too large to sufficiently exhibit the effect of the present invention that "the polypeptide is easily expressed by recombinant DNA techniques and rapidly infiltrates into the diseased area." Although the borders between adjacent domains of FLT are not clearly determined, each domain is defined herein as the one that contains the amino acid sequence designated by the following amino acid residue numbers. (The amino acid residue numbers are the same as those shown in SEQ ID NO:1. Namely, they correspond to the residue numbers counted from the amino-terminal "Ser" of the mature FLT, which is position 1 in SEQ ID NO:1.)

In the above sequences, N stands for A, C, G, or T; X or Y stands for a restriction enzyme recognition sequence; and the numeral in the parentheses indicates the number of nucleotides. Specifically, N (3–5) means that there are 3 to 5 nucleotides of A, C, G, and T, and X (6) or Y (6) indicates the recognition site for a 6-base cutter restriction enzyme. It is desirable to choose sequences that are found in neither the DNA fragment to be amplified nor the vector to which the fragment will be inserted as the restriction enzyme recognition sequences in the above. Referring to the nucleotide sequence shown in SEQ ID NO:1, the downstream primers can be appropriately designed to amplify the DNA fragments encoding the desired carboxy-termini. When inserted into an expression vector, it should be noted that the polypeptide-coding sequences must be placed under the control of a promoter sequence. Parts of the primer sequences which correspond to the flt DNA sequence do not need to be exactly limited to 21 bases, but could be about 17–25 bases. Although the condition for PCR can be a standard one as described in the "PCR Protocols" above, the reaction may be optimized to achieve a better efficiency by appropriately changing various parameters (e.g., $Mg^{2+}$ concentration, annealing temperature, extension time, the number of cycles, etc.), since the reaction proceeds differently depending on the template quantity and the primer sequences. As the DNA polymerase used for PCR, Pfu polymerase (Stratagene), which possesses a proofreading (3' exonuclease) activity, or Taq polymerase supplemented with Pfu polymerase will provide a better fidelity during the PCR amplification than Taq polymerase alone (W. M. Barnes, Proc. Natl. Acad. Sci. U.S.A., 91:2216 (1994)).

Because the sequence of the DNA fragment to be amplified by PCR is known in this case, whether the desired DNA fragment has been obtained can be determined by, after amplification, confirming its size by agarose gel electrophoresis, recovering the fragment from the gel, digesting it with appropriate restriction enzymes, and examining the resulting electrophoresis pattern. Agarose gel electrophoresis, recovering of DNA fragments from the gel, and restriction enzyme digestions can be done according to the "Molecular Cloning" above. A commercial kit which utilizes glass beads (for example, Prep-A-Gene, BIORAD) can be used for recovering DNA from a gel.

The recovered DNA fragment is digested with the restriction enzymes capable of cutting X (6) and Y (6) on both ends, deproteinated by the phenol treatment, ethanol-precipitated, and resuspended in an appropriate buffer, such as TE (10 mM Tris-HCl (pH 7.5)/1 mM EDTA). Similarly, the cloning sites of an appropriate expression vector are digested with the restriction enzymes capable of cleaving X (6) and Y (6), agarose gel electrophoresis is performed, and the vector DNA is recovered. Through this procedure, a small fragment between the X (6) and Y (6) recognition sites is eliminated. The DNA fragment to be inserted and the digested vector DNA are mixed at a ratio of, for example, vector DNA:DNA insert=1:5–1:10, and ligated using T4 DNA ligase. The ligation product is then added to competent E. coli cells, the transformation of the cells is performed, and transformants are screened by the antibiotic resistance on a culture medium containing the antibiotic corresponding to the selection marker (e.g., ampicillin resistance, kanamycin resistance, etc.) encoded by the vector.

The recombinant expression vector, to which the DNA fragment has been inserted, can be selected by examining the restriction enzyme digestion patterns of the plasmids in the antibiotic-resistant transformants. Alternatively, whether a transformant is a recombinant or not can be examined by performing a PCR reaction on the whole bacteria as the template, using the same set of primers as used to amplify the insert DNA, and detecting the presence or absence of the amplified target fragment. These series of procedures to obtain recombinant E. coli can be performed according to the "Molecular Cloning" above.

A variety of hosts can be used in order to produce the polypeptides of the present invention. For example, Gram negative and Gram positive bacteria such as Escherichia coli, bacteria belonging to the genus Pseudomonas, Bacillus subtilis, Bacillus brevis, Bacillus liqueniformis, and Bacillus thuringenesis; yeast such as Pichia pastoris, Schizosaccharomyces pombe, and Saccharoimyces cerevisiae; Eumycetes such as those belonging to the genus Aspergillus; insect cells such as Sf9 (derived from Spodoptera frugiperda), Sf21, TN5 (derived from Trichoplusia ni), and BN4 (derived from Bombyx moli); and mammalian cells such as CHO (derived from the Chinese hamster ovary) and COS (derived from the monkey kidney). The vector can be selected based on the suitability to the host cells. The final transformants may be easily obtained by producing the recombinant DNA first in E. coli using a shuttle vector functioning in the host to be used for production of the polypeptide of the present invention and E. coli. The transformations method used for obtaining the recombinant host that produces the polypeptide of the present invention include the competent cell method for E. coli; the competent cell method (K. Bott and G. A. Wilson, J. Bacteriol., 94:562 (1967)) and the protoplast method (M. Mandel and A. Higa, J. Mol. Biol., 53:159 (1970)) for bacteria belonging to the genus Bacillus; the protoplast method (M. Broker et al., BioTechniques, 5:516 (1987)) for yeast; and the lipofectin method (R. W. Malone et al., Proc. Natl. Acad. Sci. U.S.A., 86:6077 (1989)) and the calcium phosphate method (F. L. Graham and A. J. van der Eb, Virology, 52:456 (1973)) for insect cells and mammalian cells. In addition, the electroporation method (refer to the BIORAD Company's brochure) can be used with all the cell types described above.

Basically, the DNA encoding the region to be expressed can be inserted into the plasmid or viral DNA capable of replicating in the host downstream from a strong promoter that functions in the host. If the gene to be expressed is missing the translation initiation codon, it needs to be added. When a prokaryotic cell is used as the host, the ribosome binding sequence (J. R. MacLaughlin et al., J. Biol. Chem., 256:11283 (1981)) is necessary. It is also possible to apply a method using a vector, which is not replicapable in the host and contains a part of the host chromosomal DNA, to effect a homologous recombination with the host chromosome, thereby integrating the vector into the host chromosome (JP-A-Hei 4-278092, D. J. King et al., Biochem. J., 281:317 (1992)). On the other hand, animal or plant bodies may be used as hosts instead of cultured cells. For example, compared with the case that cultured cells are used as hosts, the polypeptide may be recovered from the body fluid of the silkworms more efficiently by constructing a recombinant virus from BmNPV, which is a silkworm virus, and inoculating it into silkworms (H. Kawai and Y. Shimomura, Bioindustry, 8:39 (1991)). The recombinant polypeptide may be obtained by transplanting the mouse myeloma cells transformed with a recombinant pSV vector into the abdominal cavity of a SCID or nude mouse and recovering the polypeptide from the abdominal fluid of the mouse. It may also be possible to use as hosts transgenic animals (G. Wright et al., Bio/Technology, 9:830 (1991)) or transgenic plants (M. Owen et al., Bio/Technology, 10:790 (1992)) constructed with the DNA of the present invention.

In order to secrete the polypeptide of the present invention extracellularly, the signal peptide coding region of FLT can be used as it is if a eukaryotic cell is used as the host. If a bacterium is used as the host, the DNA encoding the signal peptide of a host's secreted polypeptide may be utilized. For example, for use in E. coli host cells, signal peptide-encoding DNA can be derived from E. coli genes encoding outer membrane proteins such as OmpA or OmpF, phosphatases such as PhoA, and maltose-binding protein MalB; for use in host cells in the genus Bacillus, signal peptide-encoding DNA can be derived from Bacillus genes encoding amylases, alkaline phosphatases, and serine proteases, whose nucleotide sequences are known. If intracellular expression is desired, the signal peptide coding region except the initiation codon can be excluded. When an exogenous polypeptide is expressed at a high level in bacterial cells, inclusion bodies are often formed. If this is the case, the inclusion bodies are dissolved in an 8 M urea solution, diluted to a polypeptide concentration of several µg/ml, and then dialyzed to gradually remove the urea, thereby recovering several percents of activity of the polypeptide. It is also possible to suppress the formation of inclusion bodies by concurrently expressing E. coli thioredoxin at a high level in the bacterial cells.

The polypeptide of the present invention produced by the methods as described above can be purified through usual biochemical means, including, for example, ammonium sulfate precipitation, ion exchange chromatography, gel filtration, and hydrophobic chromatography. Since the polypeptide of the present invention has affinity to heparin, the affinity chromatography with heparin resin can be utilized. When it is produced as a fusion polypeptide with another polypeptide, it can be purified by taking advantage of the properties possessed by partner polypeptide (M. Uhlen et al., Methods Enzymol., 185:129 (1990)). For example, the purification can be carried out by affinity chromatography (F. H. Arnold, Bio/Technology, 9:151 (1991)) with protein A-Sepharose or protein G-Sepharose if the partner for the fusion polypeptide is the Fc domain of an antibody (E. Harlow and D. Lane, "Antibodies", Cold Spring Harbor Laboratory Press, 1988), with glutathione-Sepharose if it is glutathione transferase (GST) (D. B. Smith and F. S. Johnson, Gene, 67:31 (1988)), with chloramphenicol-Sepharose if it is chloramphenicol, and with $Ni^{2+}$-NTA (nitryltriacetic acid)-agarose if it is a histidine oligomer.

The fractions containing the polypeptide of the present invention can be detected by EIA or western analysis using antibodies reactive with the polypeptide. The antibodies reactive with the polypeptide of the present invention can be obtained by synthesizing the oligopeptide corresponding to the N-terminal 24–30 amino acid residues, conjugating it with carrier proteins such as bovine serum albumin and KLH (keyhole lymphet hemocyanin), and immunizing rabbits or other animals using a standard method (E. Harlow and D. Lane, "Antibodies", Cold Spring Harbor Laboratory Press, 1988). It is also possible to obtain the antibodies reactive with the polypeptide of the present invention by producing in E. coli a fusion protein of the polypeptide of the present invention and another polypeptide, purifying the fusion protein by taking advantage of the partner polypeptide's properties, and by using it as the immunogen.

Since the polypeptide of the present invention binds to VEGF, this activity can be used as an index for the purification process. For example, a solution containing the non-purified polypeptide of the present invention is appropriately diluted and a 96-well polystyrene microtiter plate is coated with the solution, followed by blocking in the same manner as in preparing a antibody-coated plate for EIA. Since the thus-obtained plate specifically binds to VEGF, the binding can be detected by measuring the residual radioactivity in the wells using the $^{125}$I-labeled VEGF. A fraction from the chromatography used for purifying the polypeptide of the present invention is preincubated with $^{125}$I-VEGF and the mixture is placed into the wells of the plate to measure the residual radioactivity. If the fraction contains the polypeptide of the present invention, its presence can be confirmed because it will bind to VEGF during the preincubation, which will cause a competition with the polypeptide of the present invention on the surface of the plate, thereby reducing the binding of VEGF to the plate.

The polypeptide of the present invention inhibits the binding of VEGF to the VEGF receptor by binding to VEGF with high affinity (Kd=approximately $5\times10^{-11}$). Therefore, the polypeptide of the present invention can inhibit the VEGF activity at a low concentration. Since the polypeptide of the present invention inhibits the VEGF activity, it blocks the proliferation of vascular endothelial cells caused by the VEGF stimulation. In addition, the polypeptide of the present invention blocks the enhancement of vascular permeability caused by VEGF. Furthermore, the polypeptide of the present invention blocks the neovascularization in vivo caused by VEGF, thereby inhibiting the tumor growth.

BRIEF DESCRIPTIOON OF THE DRAWINGS

FIG. 1 schematically shows the constitution of the extracellular domain of FLT.

FIG. 2 schematically shows the process of constructing a recombinant baculovirus that expresses 4N-FLT.

FIG. 3 schematically shows the process of constructing a recombinant baculovirus that expresses 5N-FLT.

FIGS. 7A and 7B show the autoradiography following the electrophoresis of the covalently cross-linked products between the cells infected with an EDF- or an EDFΔ11-expressing recombinant baculovirus and $^{125}$I-VEGF$_{121}$.

FIGS. 9A and 9B show the VEGF-affinity chromatogram and the electrophoresis pattern of each fraction during the EDF Δ 11 purification process.

Figure 14:
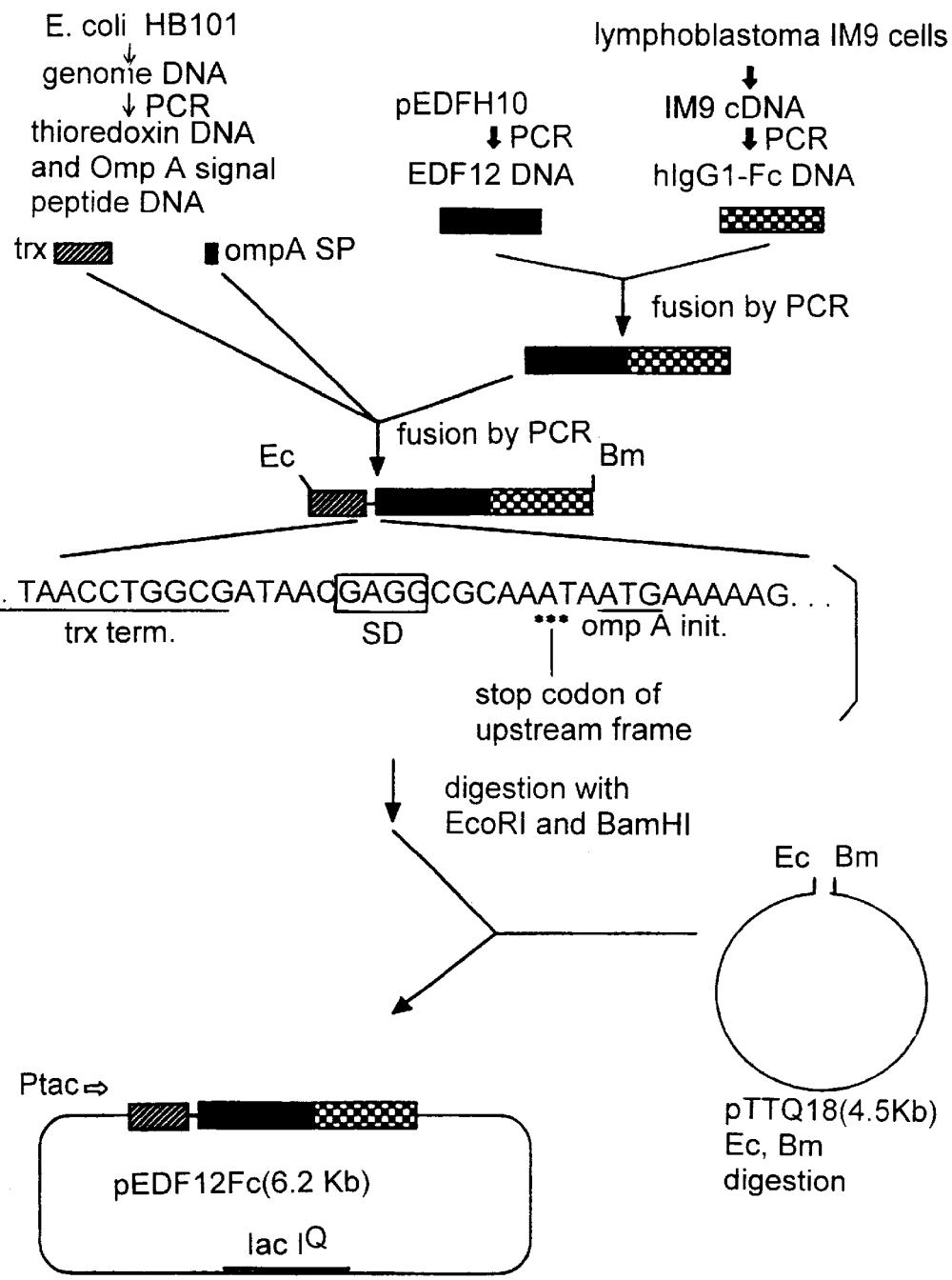

FIG. 14 schematically shows the process of constructing the recombinant FLT immunoglobulin-like domains 1&2-human $IgG_1$-Fc expression plasmid, starting from the isolation of each DNA fragment.

Figure 15:
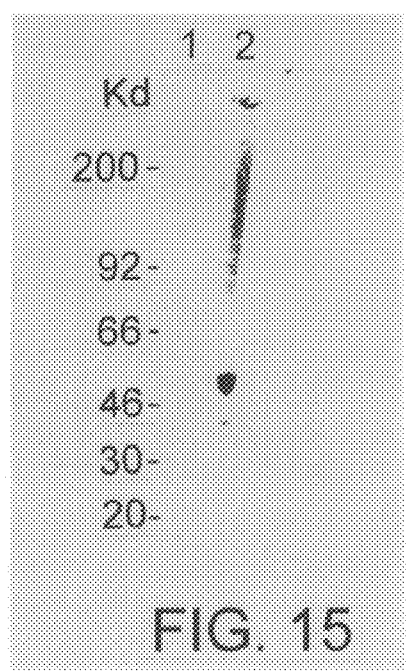

FIG. 15 shows the western blot of the recombinant E. coli crude extract by the anti-human $IgG_1$-Fc monoclonal antibody.

Figure 16:
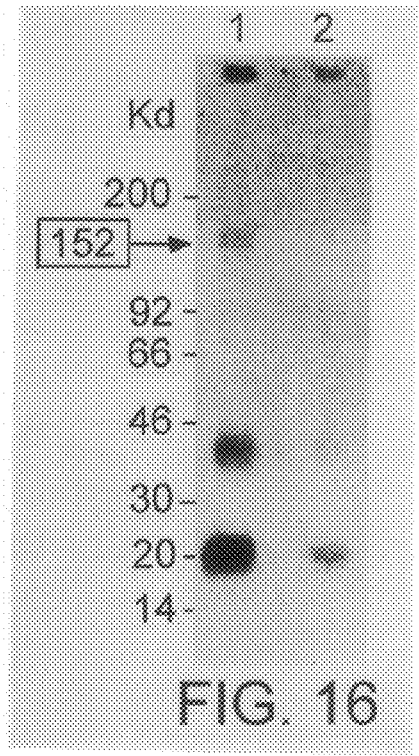

FIG. 16 shows the SDS polyacrylamide gel electrophoresis patterns of the covalently cross-linked products between the recombinant E. coli crude extract and $^{125}$I-VEGF$_{165}$.

Figure 17:
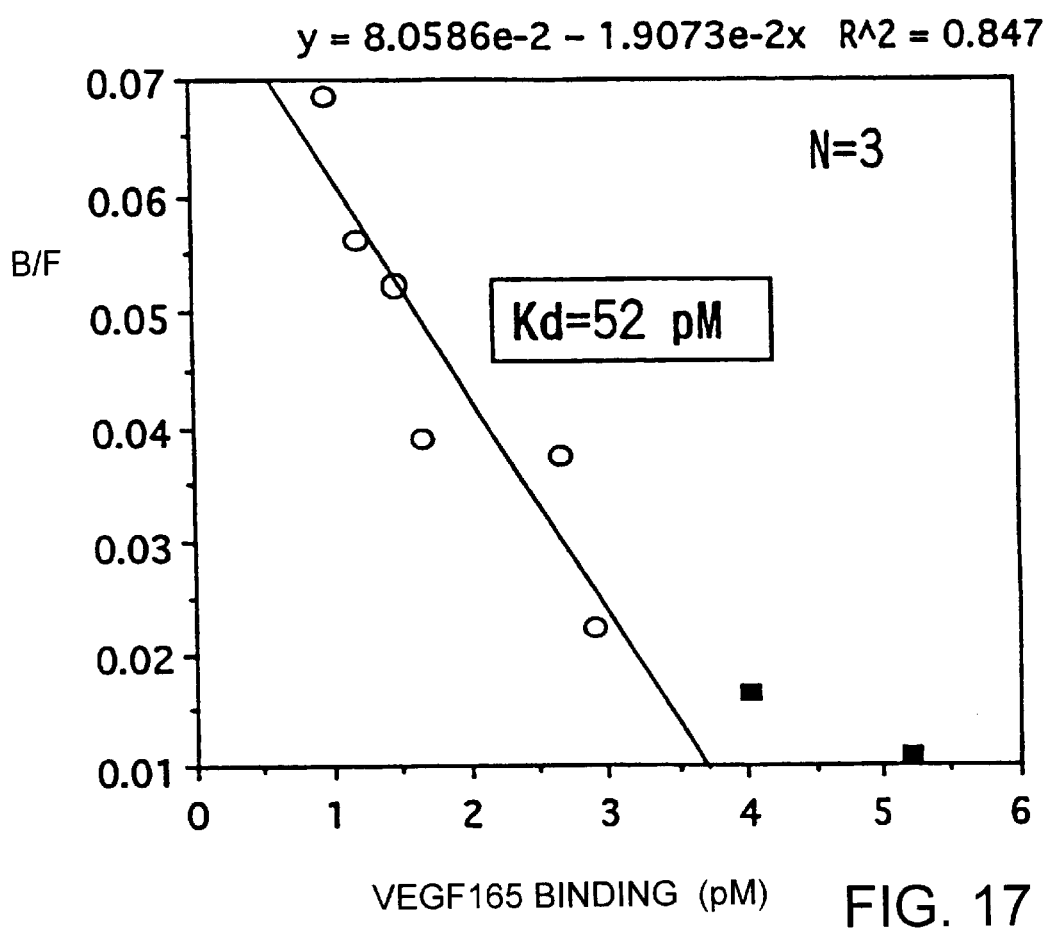

FIG. 17 shows the Scatchard analyses of the binding between the FLT immunoglobulin-like domains 1&2-human $IgG_1$-Fc fusion protein in the recombinant E. coli crude extract and $^{125}$I-VEGF$_{165}$.

Figure 18:
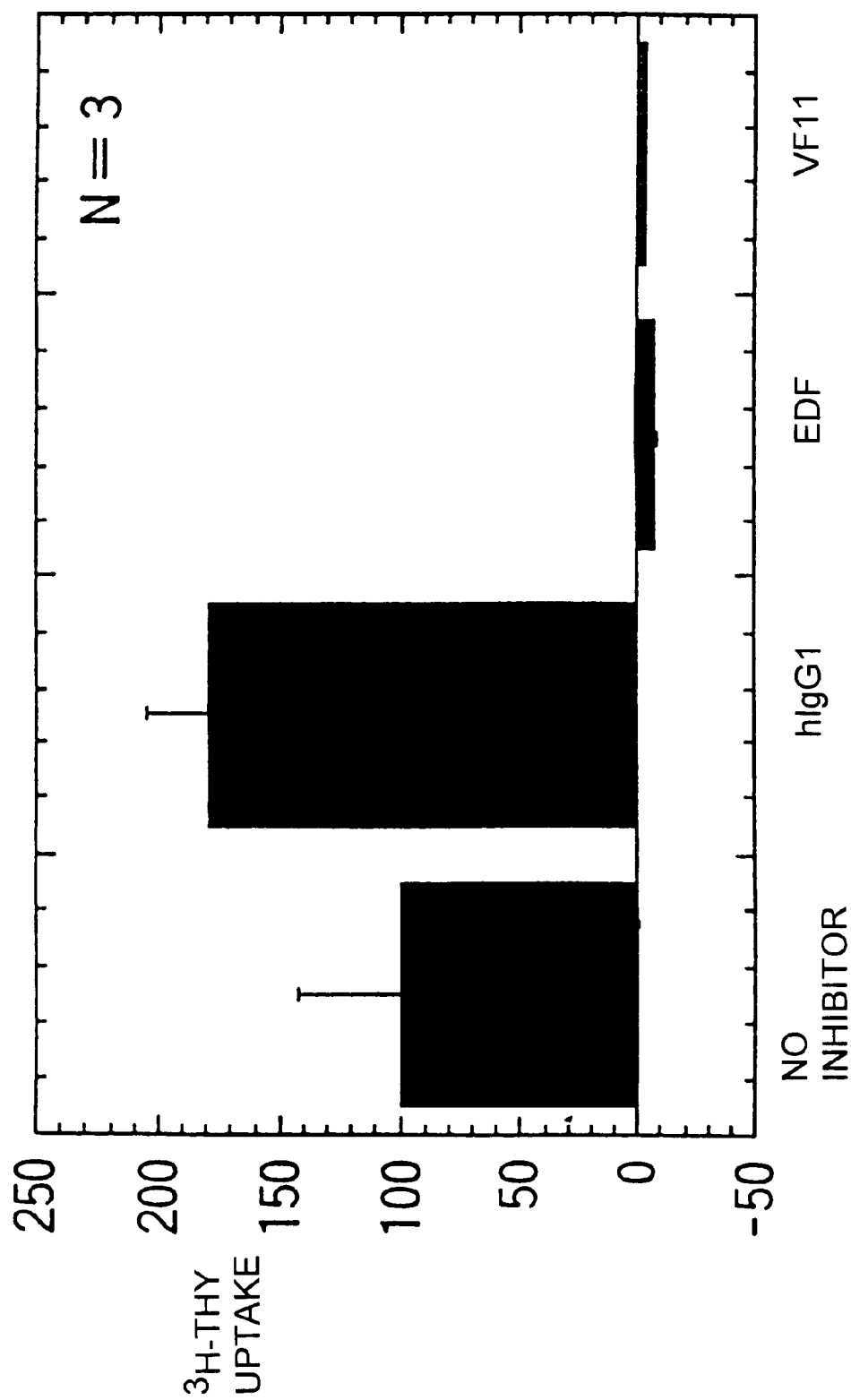

FIG. 18 shows the VEGF inhibitory activity of the partially purified FLT immunoglobulin-like domains 1&2-human $IgG_1$-Fc fusion protein.

BEST MODE FOR CARRYING OUT THE INVENTION

I. Examples Concerning the Polypeptides Comprising Immunoglobulin-like Domains 1 Through 4 or Immunoglobulin-like Domains 1 Through 5

Example 1

Construction of Recombinant Baculoviruses Expressing the Extracellular Domain of FLT 1) Construction of recombinant virus expressing immunoglobulin-like domains 1 through 4 of FLT.

Figure 2:
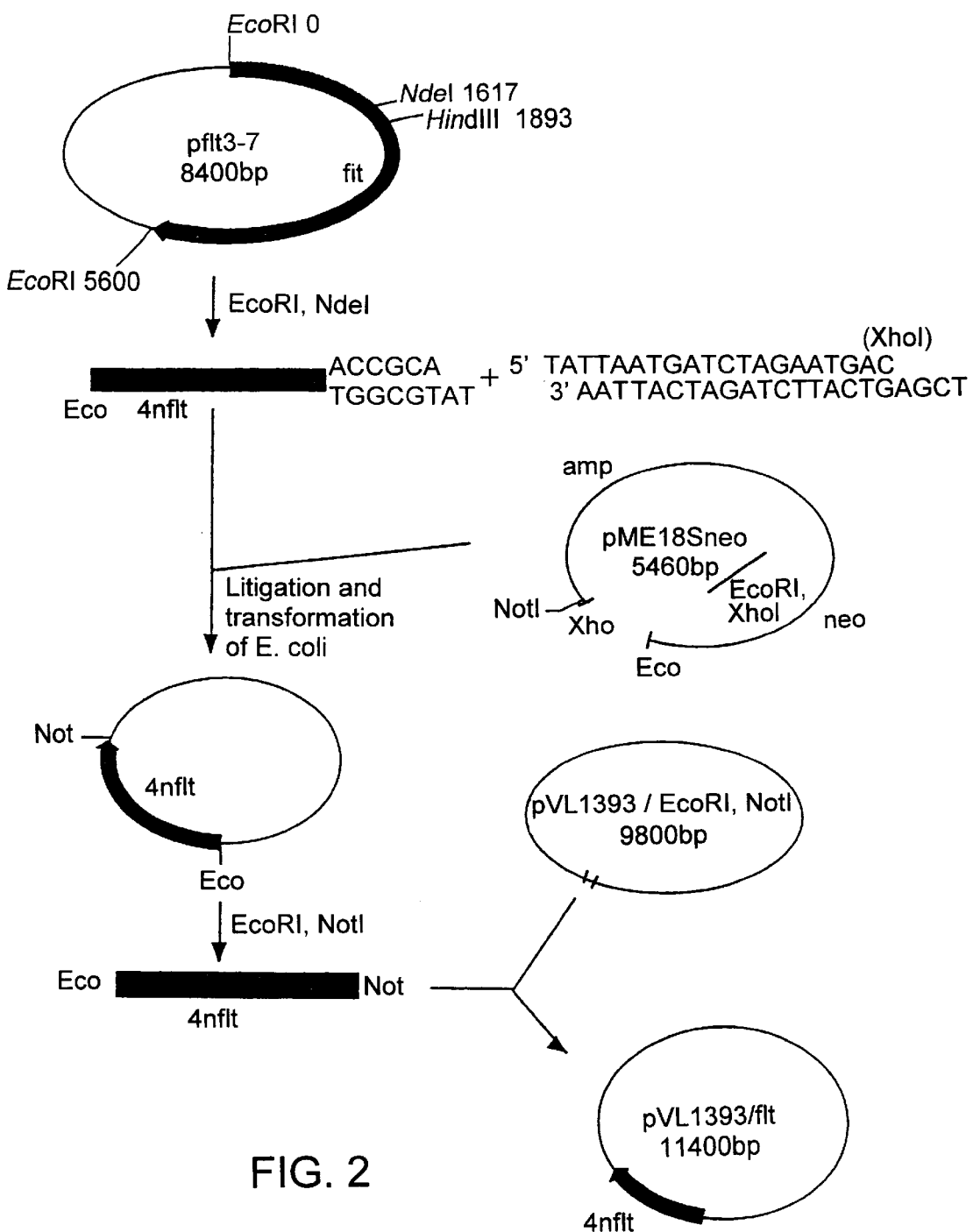

Construction of vectors was carried out following the process as shown in FIG. 2 basically according to the method described in "Molecular Cloning" by J. Sambrook et al. In order to obtain a recombinant virus expressing immunoglobulin-like domains 1 through 4 of FLT, the plasmid pflt3-7 (M. Shibuya et al., Oncogene, 5:519 (1990)) DNA was digested with restriction enzymes EcoRI and NdeI. and an EcoRI-NdeI DNA fragment of approximately 1.6 kbp was prepared following separation by agarose gel electrophoresis. Separately, the plasmid pME18Sneo DNA was digested with restriction enzymes EcoRI and XhoI, and an EcoRI-XhoI DNA fragment of approximately 5.5 kbp was prepared following separation by agarose gel electrophoresis. In order to convert the NdeI terminus into an XhoI terminus, the oligonucleotides having the following sequences, "5' TATTAATGATCTAGATGAC 3'" (SEQ ID NO:4) and "5' TCGAGTCATTCTAGATCATTAA 3'" (SEQ ID NO:5), were mixed as adapters at the room temperature, the above "1.6 kbp EcoRI-NdeI DNA fragment" and "5.5 kbp EcoRI-XhoI DNA fragment" were added thereto. Then, ligation was carried out using T4 DNA ligase and the resulting DNA was introduced into E. coli. The resulting plasmid DNA was digested with EcoRI and NotI. The 1.6 kbp fragment thus obtained was recovered and inserted into the EcoRI/NotI sites of pVL1393 (PharMingen). This plasmid DNA was purified and used to construct the recombinant virus using BaculoGold (PharMingen), which is a baculovirus DNA lacking the Polyhedrin coding region, according to the manual. This recombinant baculovirus was named "B4N." The recombinant baculovirus "B4N" was amplified in Sf9 cells according to the manual and used in the subsequent experiments. It should be noted that "B4N" contains the DNA encoding the amino acid sequence from the amino-terminus up to the 457th amino acid residue of FLT.

2) Construction of recombinant virus expressing immunoglobulin-like domains 1 through 5 of FLT.

Figure 3:
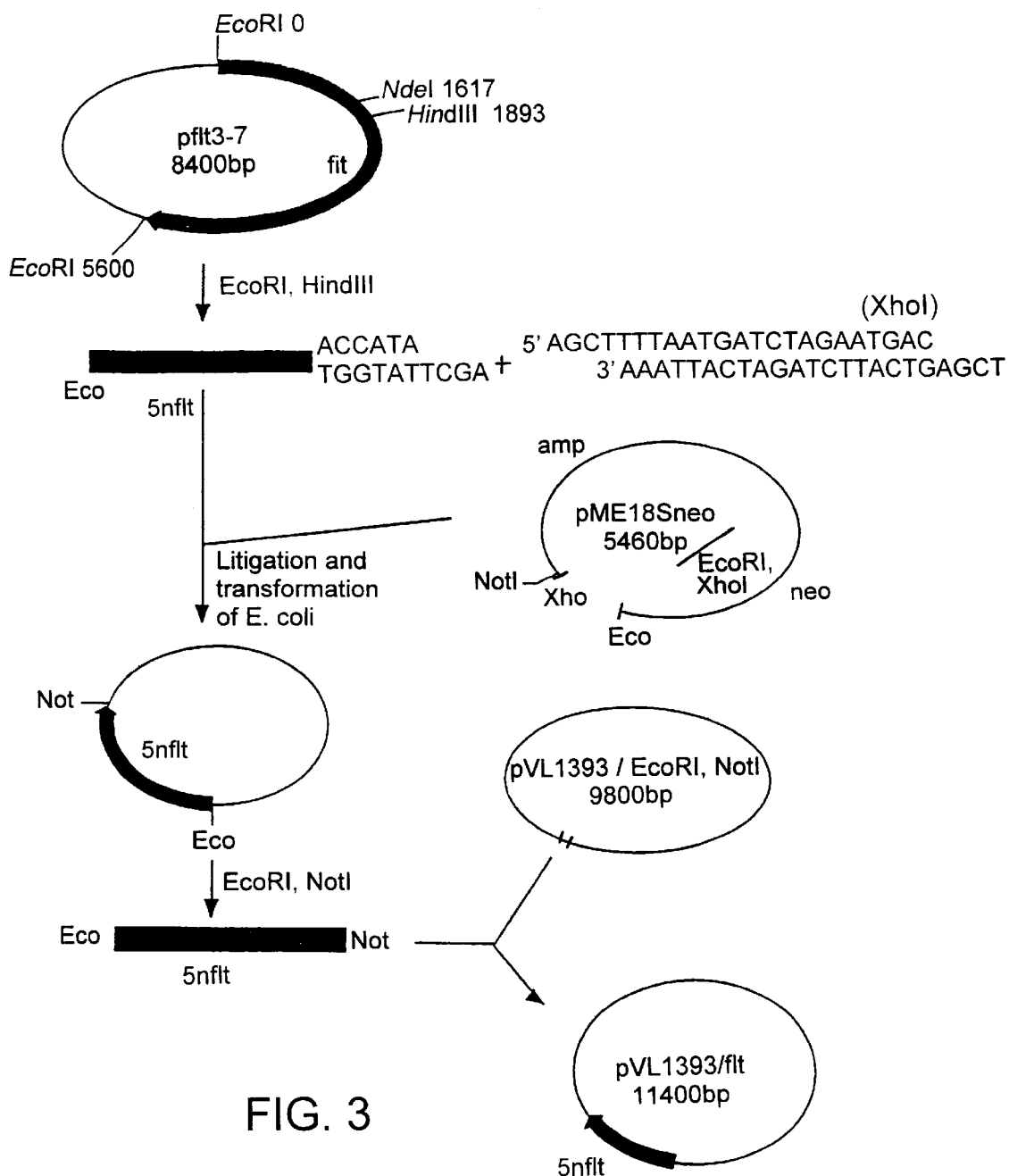

Construction of a vector was carried out following the process as shown in FIG. 3 according to the method described in "Molecular Cloning" by J. Sambrook et al. The plasmid pflt3-7 DNA was digested with EcoRI and HindIII, and a 1.9 kbp EcoRI-HindIII DNA fragment was prepared. In order to convert the HindIII terminus into an XhoI terminus, the oligonucleotides having the following sequences, "5' AGCTTTTAATGATCTAGAATGAC 3'" (SEQ ID NO:6) and "5' TCGAGTCATTCTAGATCAT-TAAA 3'" (SEQ ID NO:7), were mixed as adapters and added to the above fragment to ligate with the 5.5 kbp EcoRI-XhoI DNA fragment from the plasmid pME18Sneo described above. The resulting ligation product was used to transform E. coli cells to give a recombinant plasmid. The resulting plasmid DNA was digested with EcoRI and NotI, and the 1.9 kbp fragment thus produced was recovered and inserted into the EcoRI/NotI sites of pVL1393 (PharMingen). This plasmid DNA was purified and used to construct the recombinant virus using BaculoGold (PharMingen), which is a baculovirus DNA lacking the Polyhedrin coding region, according to the manual. This recombinant baculovirus was named "B5N." The recombinant baculovirus "B5N" was amplified in Sf9 cells according to the manual and used in the subsequent experiments. It should be noted that "B5N" contains the DNA encoding the amino acid sequence from the amino-terminus up to the 560th amino acid residue of FLT.

Example 2
Immunochemical Analysis of Expression Products

Figure 4:
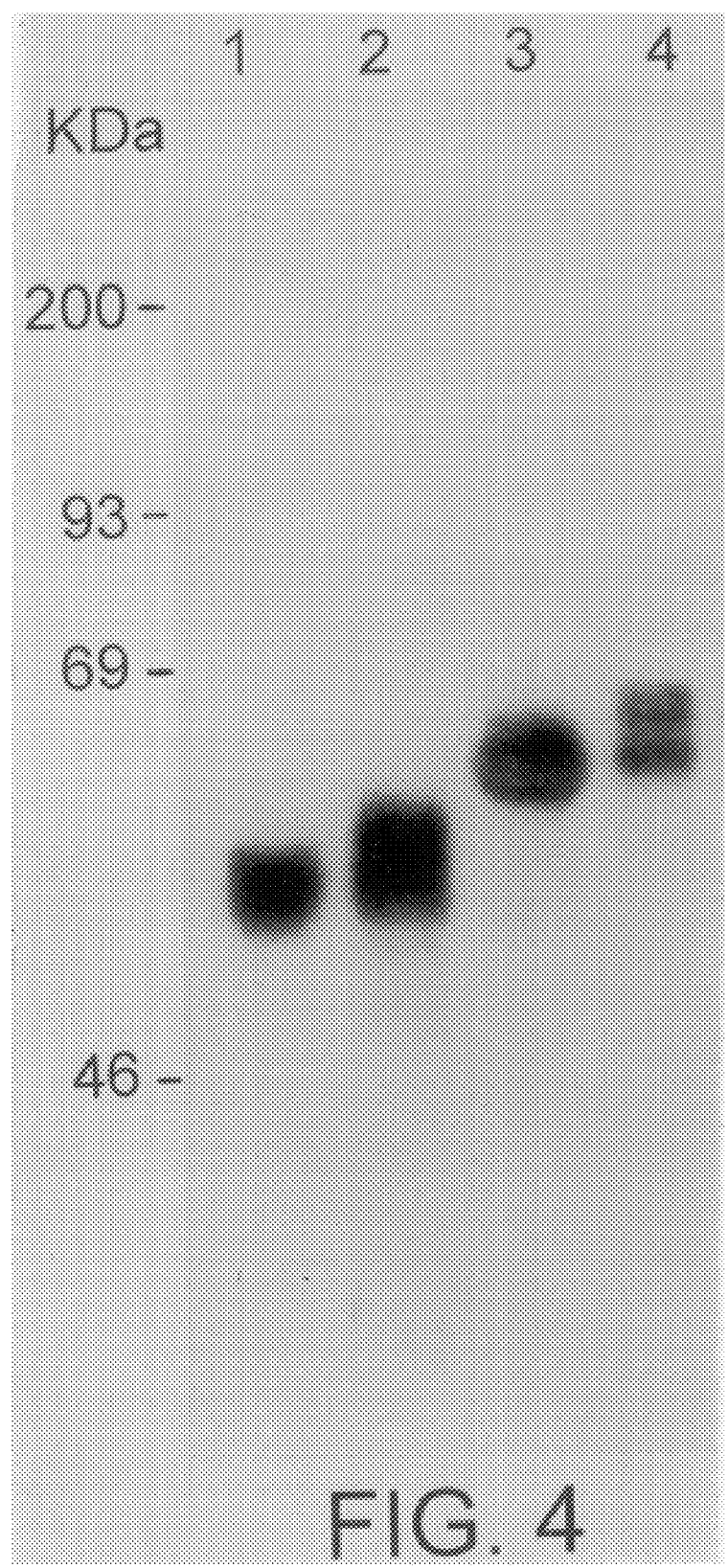
FIG. 4 shows the results of the western blotting using the culture supernatants and the extracts of the cells infected with the recombinant B4N or B5N baculovirus.

HIFive™ insect cells (manufactured by Invitrogen Corp.) were cultured in the EXCELL 400™ culture medium (manufactured by Iwaki Glass) and infected with the recombinant baculovirus "B4N" or "B5N". The culture supernatants were recovered and electrophoresed on an SDS-polyacrylamide gel, followed by western blotting. A rabbit anti-FLT extracellular domain polyclonal antibody was used as the primary antibody and the alkaline phosphatase-labeled anti-rabbit IgG as the secondary antibody to develop color by adding NTB (Nitroblue tetazolium chloride)/BCI P (5-Bromo-4-chloro-3-indolylphosphate p-toluidine salt) (manufactured by Gibco BRL). The results indicated specific reactivity with this antibody (FIG. 4). Lane 1 stands for the electrophoretic pattern of 2 μl of the culture supernatant of B4N-infected cells, lane 2 for 10 μl of the extract of B4N-infected cells, lane 3 for 2 μl of the culture supernatant of B5N-infected cells, and lane 4 for 10 μl of the extract of B5N-infected cells. The mobility of the bands exhibiting the immunochemical reactivity was in agreement with their expected molecular weights. Hereinafter these products were called "4N-FLT" and "5N-FLT," respectively. It was estimated that the culture supernatant samples contained approximately 2 μg/ml of "4N-FLT" or "5N-FLT."

Example 3
Affinity of Expression Products for VEGF

Figure 5A:
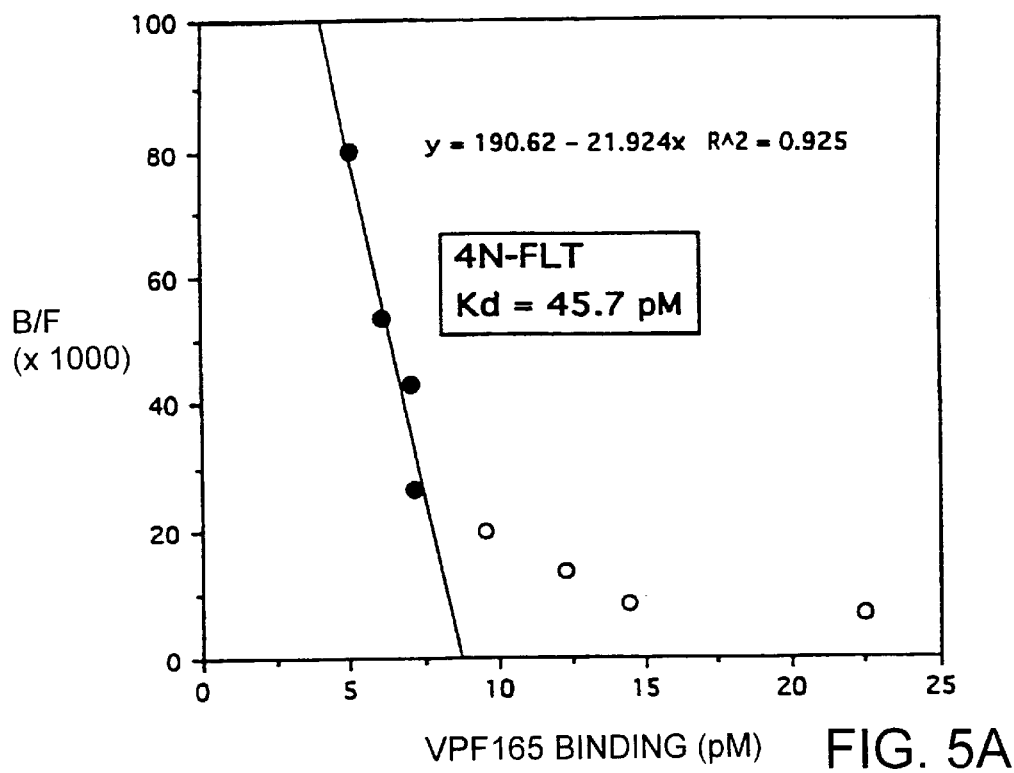
FIGS. 5A and 5B show the Scatchard analyses of the interactions between 4N-FLT or 5N-FLT and the VEGF fragment.
Figure 5B:
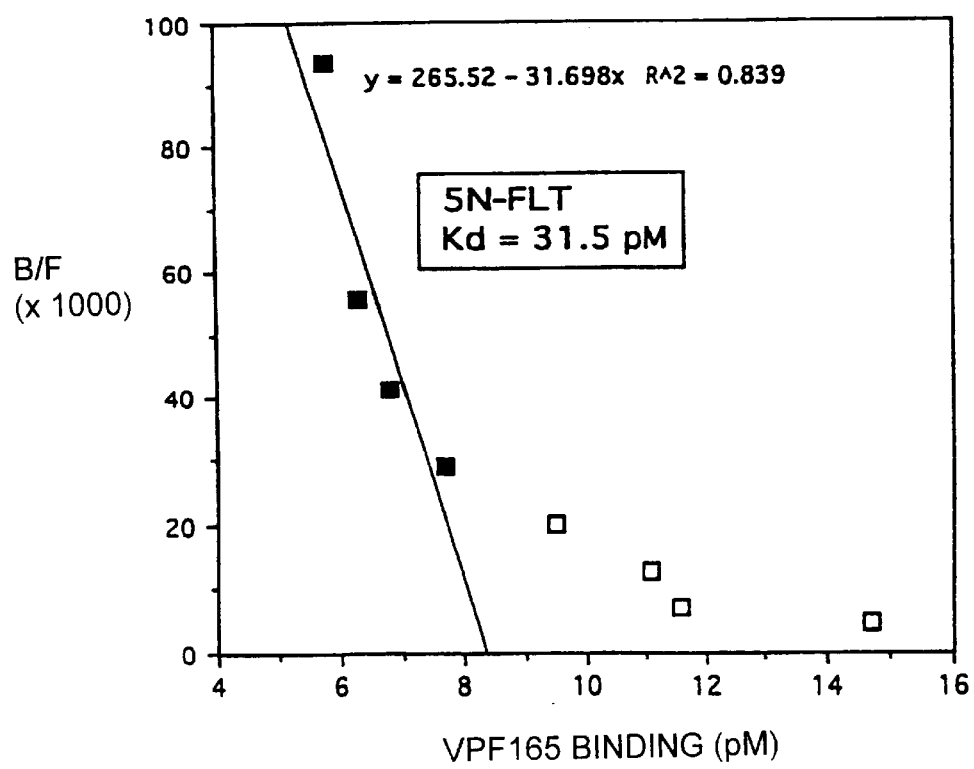

HIFive™ cells were infected with the recombinant virus "B4N" or "B5N". The recovered supernatants were diluted 4 times with PBS, 100 μl portions of which were dispensed into each well of a microtiter plate ("Immuron 2" manufactured by Dynatech). After the plate was kept overnight at 4° C., the liquid was removed from the wells and the wells were washed 3 times with PBS-0.1% BSA. Then, 250 μl of PBS-1% BSA was added thereto and the plate was left at room temperature for 2 hr for blocking. The wells were emptied followed by adding 100 μl of a solution prepared by mixing 20,280 cpm of the $^{125}$I-VEGF$_{165}$ (a peptide corresponding to the amino-terminus and up to the 165th residue of VEGF/manufactured by Amersham) having specific activity of 66,000 cpm/ng with 0–15,000 pg of unlabeled VEGF$_{165}$. The plate was left at room temperature for 3 hr. The wells were then emptied and washed 3 times with PBS-0.1% BSA. The residual radioactivity in the wells was measured by a Acounter for Scatchard analysis (FIG. 5). FIGS. 5A and 5B correspond to the results from the plates coated with the "B4N" and "B5N" expression culture supernatants, respectively. Since $^{125}$I-VEGF$_{165}$ hardly binds to the plate coated with the culture supernatant from the control virus-infected Sf9 cells, the bound radioactivity can be considered to result from the binding of $^{125}$I-VEGF$_{165}$ to the inserted gene expression products. The affinity for VEGF$_{165}$ of the expression products in the culture supernatants of the "B4N"- or "B5N"- infected cells was calculated in Kd (dissociation constant) of approximately $3$–$4.5 \times 10^{-11}$, which was close to the values reported for FLT (J. Waltenberger et al., J. Biol. Chem., 269:26988 (1994)) or soluble FLT (R. L. Kendal and K. A. Thomas, Proc. Natl. Acad. Sci. U.S.A., 90:10705 (1993)).

Example 4
Inhibition of Biological Activities of VEGF by the Expression Products 1) Inhibition of the permeability enhancing activity of VEGF. The inhibitory effect of "4N-FLT" or "5N-FLT" on the permeability enhancing activity of VEGF was examined. Namely, 0.5 ml of 1% Evans Blue dye solution was injected into the heart of a guinea pig. Thirty minutes later, 0.2 ml of "4N-FLT" or "5N-FLT" expression culture supernatant was injected into the shaved skin portion together with VEGF and the leakage of the dye was observed 30 min thereafter (Table 1). The results clearly indicated that "4N-FLT" and "5N-FLT" inhibited the permeability enhancing activity of VEGF.

TABLE 1

Inhibitory effect of "4N-FLT" and "5N-FLT" on permeability enhancing activity of VEGF

| Samples | Dye leakage (relative value) |
| --- | --- |
| PBS | 0% |
| 10 ng VEGF/0.2 ml | 100% |
| 10 ng VEGF + Ca. 400 ng 4N-FLT/0.2 ml | 5% |
| 10 ng VEGF + Ca. 400 ng 5N-FLT/0.2 ml | <5% |

2) Inhibition of VEGF-dependent proliferation of rat sinusoidal endothelial cells.

The inhibitory effect of "4N-FLT" or "5N-FLT" on VEGF-dependent proliferation was examined. The sinusoidal endothelial cells were prepared from the rat liver according to the method as described and inoculated at $10^4$ cells/well onto 24-well plates. The cells were cultured for 4 days in the presence of the samples listed in Table 2 and the cells in each well were counted. The numerals in the column of the cell number in Table 2 stand for relative values with taking the number of cells immediately after the inoculation as 100. For "4N-FLT" and "5N-FLT" samples, the corresponding recombinant virus-infected HiFive culture supernatants were used and the concentrations were calculated based on the results of the western analysis. The results indicate that "4N-FLT" and "5N-FLT" inhibit the VEGF's endothelial cell proliferation activity dose-dependently.

TABLE 2

VEGF-dependent proliferation inhibition activity of "4N-LFT" and "5N-LFT" on rat liver sinusoidal endothelial cells

| VEGF concentration (ng/ml) | 4N-FLT concentration (ng/ml) | 5N-FLT concentration (ng/ml) | Cell number |
| --- | --- | --- | --- |
| 0 | 0 | 0 | 0 |
| 1 | 0 | 0 | 260 |
| 1 | 40 | 0 | 40 |
| 1 | 100 | 0 | 44 |
| 1 | 0 | 40 | 27 |
| 1 | 0 | 100 | 28 |
| 3 | 0 | 0 | 300 |
| 3 | 40 | 0 | 191 |
| 3 | 100 | 0 | 69 |
| 3 | 0 | 40 | 21 |
| 3 | 0 | 100 | 83 |

II. Eamples Concerning the Polypeptides Comprising Immunoglobulin-like Domains 1 and 2

Example 5
Production of Polyclonal Antibodies Reactive with the Extracellular Domain of FLT (EDF)

1) Preparation of cDNA from human umbilical cord-derived vascular endothelial cells (HUVEC).

One ml of ISOGEN (manufactured by Wako Pure Chemical Industries) was added to approximately $1 \times 10^7$ HUVEC cells (manufactured by Kurabo) and the cells were disrupted with a pestle. Further, 9 ml of ISOGEN was added thereto followed by shaking for 5 min. After adding 1 ml of chloroform to this solution, the mixture was shaken for 1 min and centrifuged at 10,000 rpm for 10 min to recover the supernatant, to which 1/10 vol of 3 M sodium acetate (pH 5.2) was added. To the resulting mixture was added 2.5 vol of ethanol to recover the precipitate following centrifugation. The precipitate was washed with 75% ethanol, dried, and dissolved in 100 µl heat-sterilized pure water. Thus, 102 µg of RNA was obtained. To this solution were added 1 µl of 10% SDS and 100 µl of "Oligotex-dT30 (manufactured Takara Shuzo)". The resulting mixture was incubated at 65° C. for 5 min and then rapidly cooled in ice. This solution was mixed with 20 µl of 5 M sodium chloride and incubated at 37° C. for 10 min. The suspension thus obtained was centrifuged at 15,000 rpm for 15 min to recover the precipitate, which was resuspended in 100 µl of heat-sterilized pure water and incubated at 65° C. for 5 min. The suspension was centrifuged at 15,000 rpm for 15 min to recover the supernatant followed by ethanol precipitation. The dried precipitate was dissolved in 20 µl of heat-sterilized pure water. The resulting product was designated as HUVEC poly(A)$^+$ RNA. Subsequently, 100 µl of the HUVEC double-stranded cDNA solution primed by oligo dT was obtained using this solution and the cDNA synthesis kit manufactured by Pharmacia following the manual.

2) Cloning of DNA encoding the FLT extracellular domain (EDF).

Using the HUVEC-derived cDNA obtained in 1) as the template, PCR was performed with the following conditions.

TABLE 3

| Composition of the reaction mixture (in 100 µl) | Reaction condition |
| --- | --- |
| 10 µl Taq buffer (Promega) | 1) 95° C., 1 min; 1 cycle |
| 2.5 mM MgCl$_2$ | 2) 94° C., 1 min; 56° C., 1 min; |
| 4 µl HUVEC cDNA | 72° C., 2.5 min; 34 cycles |
| 0.1 mM each dNTPs | 3) 72° C., 7 min; 1 cycle |
| 200 nM primer 1 | |
| 200 nM primer 2 | |
| 2.5 U Taq polymerase (Promega) | |

The primer sequences are as follows:

Primer 1:
5'-CTCGGATCCGA<u>TCTAGTTCAGGTTCAAAA</u>-3'    (SEQ ID NO:8)

Primer 2:
5'-CTCGAATTCA<u>CTCCAGATTAGACTTGTCCGA</u>-3'    (SEQ ID NO:9)

The underlined portion of "Primer" 1 corresponds to the N-terminal coding sequence of the mature FLT, and that of "Primer 2" corresponds to the C-terminal coding sequence of the FLT extracellular domain.

Two hundred µl of the reaction mixture was treated with an equal volume of chloroform in order to remove the mineral oil and the aqueous layer was recovered, to which 4 µl of 10% SDS was added. After incubation at 60° C. for 5 min, the solution was treated with an equal volume of TE-saturated phenol, an aqueous layer was recovered followed by ethanol precipitation to recover the DNA fragment. The dried precipitate was dissolved in 30 µl of TE and subjected to agarose gel electrophoresis. A DNA fragment of approximately 2.2 kbp was excised from the gel, and the DNA was recovered using a Prep-A-Gene™ Kit (manufactured by BIORAD) according to the manual. The recovered DNA was digested with HincII, HindIII, HhaI, or PstI to confirm the digestion patterns were in agreement with the patterns expected from the nucleotide sequence of the FLT extracellular domain encoding DNA. This DNA fragment was then digested with EcoRI and BamHI, the resulting reaction mixture was treated with an equal volume of TE-saturated phenol, and the EcoRI, BamHI-digester DNA fragment was recovered from the aqueous layer using a Prep-A-Gene™ Kit. Similarly, 1 μg of plasmid A vector pGEX2T (manufactured by Pharmacia Biosystem) was digested with EcoRI and BamHI, the resulting reaction mixture was treated with an equal volume of TE-saturated phenol, and the EcoRI, BamHI-digested pGEX2T DNA was recovered from the aqueous layer using "Prep-A-Gene."

The DNA fragment and the plasmid DNA thus obtained were mixed at a molar ratio of 10:1 and ligation was performed (Ligation Kit manufactured by Takara Shuzo). *E. coli* JM109 competent cells (manufactured by Takara Shuzo) were transformed by this ligation mixture, plated onto the 2×TY culture medium (trypton 16 g, yeast extract 10 g, sodium chloride 5 g, and agar 1.5 g per 1 liter) containing 75 μg/ml ampicillin, and cultured overnight at 37° C. The ampicillin-resistant colonies that emerged on the plate were picked up with toothpicks, transferred into 15 μl of the PCR reaction mixture which was identical to the above-described one except for lacking the template to perform PCR as described above for 30 cycles. After the PCR, the reaction mixture was subjected to agarose gel electrophoresis, single colonies were isolated from the ones that produced a 2.2 kbp band and the plasmid DNA was prepared from a small quantity of the culture medium (according to the procedures described in J. Sambrook et al., "Molecular Cloning," Cold Spring Harbor Laboratory Press, 1989). These plasmid DNAs were digested with BamHI and EcoRI and it was confirmed that they generated a 2.2 kbp fragment. One of these plasmid DNAs was sequenced using the above "Primer 1"0 or "Primer 2" (according to the procedures described in J. Sambrook et al., "Molecular Cloning," Cold Spring Harbor Laboratory Press, 1989) and approximately 150 nucleotides upstream and downstream from the fragment were examined. As a result, the sequence of the fragment was confirmed to be identical to the nucleotide sequence of the FLT extracellular domain (EDF) coding DNA.

3) Preparation of the GST-EDF fusion polypeptide.

The *E. coli* clone, which contains the above plasmid whose partial nucleotide sequence was confirmed, was shake-cultured at 30° C. in 500 ml of the 2×TY culture medium containing 50 μg/ml ampicillin. IPTG was added to give the final concentration of 0.1 mM when the absorbance at 600 nm reached 1.0 and the medium was further cultured for another 20 hr. The cells were recovered by centrifugation and about 7.1 mg of the GST-EDF fusion polypeptide. with a purity of approximately 60% was prepared using glutathione-Sepharose (Pharmacia Biosystem) according to the procedure described in the manual. As a result of SDS-polyacrylamide gel electrophoresis according to Laemmli, the fusion polypeptide had a molecular weight of 60,000, from which the molecular weight of the GST of 28,000 was subtracted to give the partner for the fusion polypeptide of the molecular weight of about 32,000. Since the binding ability of GST to glutathione-Sepharose suggested that the GST portion was hardly decomposed, the latter half of EDF was presumed to have been lost, leaving the N-terminal portion with the molecular weight of 32,000.

4) Preparation of antibodies against the GST-EDF fusion polypeptide.

The GST-EDF fusion polypeptide prepared in 3) above was mixed with Freund's complete adjuvant and subcutaneously injected to rabbits in a dose of initially 200 μg and subsequently 100 μg every other week per animal for a total of seven times. A measurement of titer using antigen-coated plates revealed that the sera possessed sufficient immunological reactivity after more than 64,000-fold dilution. Thus, 150 mg of the IgG fraction was obtained from the sera of two rabbits according to the procedures described in "Antibodies" by E. Harlow and D. Lane.

Example 6

Production of Recombinant Baculoviruses Expressing EDF and the Fragments Thereof.

1) Construction of a recombinant transfer vector for the production of recombinant baculoviruses expressing EDF and the fragments thereof.

PCR was performed with the plasmid pflt3-7 (M. Shibuya et al., Oncogene, 5:519 (1990)) as the template under the following conditions.

TABLE 4

| Composition of the reaction mixture (in 100 μl) | Reaction condition |
|---|---|
| 10 μl Pfu buffer #1 (Stratagene) | 1) 95° C., 1 min; 55° C., 1 min; 75° C., 2.5 min; 3 cycles |
| 1 μg pflt3-7 | 2) 94° C., 1 min; 55° C., 1 min; |
| 0.1 mM dNTPs | 75° C., 2.5 min; 30 cycles |
| 200 nM primer 3 | 3) 75° C., 5 min; 1 cycle |
| 200 nM primer 4 | |
| 5 U Pfu polymerase (Stratagene) | |

The sequences of the primers used in the above reaction were as follows:

```
Primer 3:
    5'-TTTCTCGGATCCTATAAATATGGTCAGCTACTGGGACACC-3'        (SEQ ID
                                                          NO:10)

Primer 4:
    5'-GTGGTGGTGGTGGTGGTGACGCTCCAGATTAGACTTGTCCGA-3'      (SEQ ID
                                                          NO:11)
```

The underlined portion of "Primer 3" corresponds to the N-terminal coding sequence of the mature FLT and that of "Primer 4" corresponds to the C-terminal coding sequence of the FLT extracellular domain.

In order to obtain a DNA fragment containing the polyadenylation signal, PCR reaction was performed under the following conditions using the plasmid pRc/RSV (manufactured by Invitrogen Corp.) as the template to give a DNA (0.3 kbp) containing the polyadenylation signal derived from the bovine growth hormone gene.

TABLE 5

| Composition of the reaction mixture (in 100 μl) | Reaction condition |
|---|---|
| 10 μl Pfu buffer #1 (Stratagene) | 1) 95° C, 1 min; 55° C., 1 min; 75° C., 0.5 min; 3 cycles |
| 1 μg pRc/RSV | 2) 94° C., 1 min; 55° C., 1 min; |

TABLE 5-continued

| Composition of the reaction mixture (in 100 μl) | Reaction condition |
| --- | --- |
| 0.1 mM dNTPs<br>200 nM primer 5<br>200 nM primer 6<br>5 U Pfu polymerase (Stratagene) | 75° C., 0.5 min; 30 cycles<br>3) 75° C., 5 min; 1 cycle |

The sequences of the primers used in the above reaction were as follows:

```
Primer 5:
     5'-CACCACCACCACCACCACTAACTAGAGCTCGCTGATC-3'   (SEQ ID
                                                   NO:12)

Primer 6:
     5'-TTCTCGAATTCTCCCCAGCATGCCTGC-3'             (SEQ ID
                                                   NO:13)
```

The underlined portions of "Primer 5" and "Primer 6" correspond to the sequences upstream and downstream of the polyadenylation signal derived from the bovine growth hormone gene in pRc/RSV.

A 200 μl portion of each reaction mixture thus obtained was treated with an equal volume of chloroform and the aqueous layer was recovered. Reagents were added thereto to make their final concentrations be 0.5% for SDS, 0.1 M for Tris-HCl (pH 6.8), 5 mM for EDTA, and 200 μg/ml for proteinase K. The solutions were incubated at 37° C. for 30 min. These solutions were treated with TE-saturated phenol, the aqueous layers were subjected to ethanol precipitation, and the DNA fragment encoding EDF and the DNA containing the polyadenylation signal were dissolved in TE. These DNA solutions were subjected to agarose gel electrophoresis to recover the 2.2 kbp and 0.3 kbp fragments from the respective gel, which were each dissolved in 50 μl of a TE solution. Then another PCR reaction was performed under the following conditions in order to fuse these DNA fragments via PCR (R. Higuchi, "PCR Protocols," Academic Press Inc., 177 (1990)).

TABLE 6

| Composition of the reaction mixture (in 100 μl) | Reaction condition |
| --- | --- |
| 10 μl Pfu buffer #1 (Stratagene)<br>4 μl EDF coding DNA<br>0.25 μl poly A signal DNA<br>0.1 mM dNTPs<br>200 nM primer 3<br>200 nM primer 6<br>5 U Pfu polymerase (Stratagene) | 1) 95° C., 1 min; 58° C., 1 min;<br>75° C., 0.5 min; 3 cycles<br>2) 94° C., 1 min; 55° C., 1 min;<br>75° C., 0.5 min; 30 cycles<br>3) 75° C., 5 min; 1 cycle |

Two hundred μl of the reaction mixture thus obtained was treated with an equal volume of chloroform and the aqueous layer was recovered. Reagents were added thereto make their final concentrations to be 0.5% SDS, 0.1 M Tris-HCl (pH 6.8), 5mM EDTA, and200 μg/ml proteinase K followed by incubation at 37° C. for 30 min. The solution was treated with TE-saturated phenol, the aqueous layer was subjected to ethanol precipitation, and the DNA was dissolved in TE. The DNA solution was subjected to agarose gel electrophoresis to recover the 2.5 kbp DNA fragment considered to be the fusion product between the DNA fragment encoding EDF and the DNA fragment containing the polyadenylation signal, which was dissolved in 50 μl of a TE solution. A DNA fragment was prepared by digesting the both ends of this DNA fragment with BamHI and EcoRI. Separately, 1 μg of the plasmid pVL1393 (PharMingen), which is a transfer vector for the recombinant baculovirus, was digested with BamHI and EcoRI to prepare the BamHI-EcoRI fragment following the method described in the Example 5-2). This plasmid DNA was mixed with the DNA fragment encoding EDF, which was obtained by the PCR amplification of plasmid pflt3-7 followed digestion with BamHI and EcoRI, at a molar ratio of approximately 1:5 and treated with the Ligation Kit (manufactured by Takara Shuzo). The ligation product was used to transform competent E. coli JM109 cells and six clones containing the recombinant plasmid were selected using a method similar to the one described in Example 5-2). Plasmid DNA was prepared from a 3 ml culture of each clone by the alkali method and the nucleotide sequence was determined for about 300 bp upstream and about 500 bp downstream of the inserted fragment. As a result, the plasmids derived from two different kinds of clones had the correct sequences. These plasmids were designated "pEDFH10" and "pEDFH11." The E. coli cells harboring these plasmids were cultured in 100 ml of the 2×TY medium containing 50 μg/ml ampicillin overnight at 37° C. The plasmid DNAs were extracted from the recovered cell bodies using the alkali method (according to J. Sambrook et al., "Molecular Cloning," Cold Spring Harbor Laboratory Press, 1989), purified with an ion exchange column according to the manual (Diagen GimbH manufactured by Qiagen), and dissolved in 200 μl each of TE, to give approximately 100 μg each of plasmid DNA.

2) Production of recombinant baculoviruses expressing EDF and the fragments thereof.

Sf9 cells (manufactured by Invitrogen Corp.) cultured in the TMN-FH medium (manufactured by PharMingen) at an 80% confluency were detached by pipetting, inoculated at $2 \times 10^6$ cells per 60 mm dish, and allowed to adsorb onto the surface by standing for 30 min. Then, the medium was replaced with 2 ml of Ex-Cell 400 (manufactured by Iwaki Glass), which is a serum-free medium. Sixteen μl of the solution containing 8 μl (4 μg) of "pEDFH10" or "pEDFH11" and 2 μl (40 ng) of the deleted baculovirus DNA (BaculoGold manufactured by PharMingen) was mixed with 16 μl of the solution made by diluting Lipofectin two-fold in sterilized pure water. After the mixture was allowed to stand for 15 min, the total volume of 32 μl was added to the above-described dish and mixed. The dishes were shake-cultured in a humidified box at 27° C. for 6 hr at 30 rpm, and were stationary-cultured at 27° C. for 5 days after replacing the medium with 2.5 ml TMN-FH. The media were recovered and the supernatants obtained by centrifugation were prepared as the original virus stocks (designated "BEDFH10" and "BEDFH11" respectively). The plaque assay performed according to the manual of Invitrogen Corp. revealed that both of these viruses had a titer of approximately $3 \times 10^6$. For each virus, two clones ("BEDFH101" and "BEDFH102" from "BEDFH10" and "BEDFH111" and "BEDFH112" from "BEDFH11) were obtained by plaque isolation followed by 4-step amplifications according to the manual of Invitrogen Corp. to give about 200 ml of the virus solution (having a titer of about $5 \times 10^7$/ml).

Example 7

Analysis of the Expression Products from the Recombinant Virus-infected Sf9 Cells 1) Covalently cross-linked products with $^{125}$I-VEGF$_{121}$.

To $2 \times 10^5$ Sf9 cells infected with the above recombinant viruses at m.o.i. of 0.3 (m.o.i. means the ratio of virus particles to cell number) was added 180,000 cpm of $^{125}$I-VEGF$_{121}$ (150,000 cpm/ng) and incubated in 100 μl of PBS-0.1% BSA for 1 hr at room temperature. After washing twice with the same buffer by centrifugation, the cells were again suspended in 100 μl of PBS-0.1% BSA. This solution was mixed with 1/10 volume of 50mM disuccinylsuberate/dimethylsulfoxide, and, after incubation at room temperature for 40 min, 1/10 volume of 1 M Tris-HCl (pH 6.8) was added. These samples were subjected to SDS-polyacrylamide gel electrophoresis under reducing conditions according to Laemmli and the signal was detected by autoradiography (FIG. 7). From the cells infected with the two clones isolated from "BEDFH10," which is the recombinant virus constructed using plasmid "pEDFH10, " a covalently cross-linked product of molecular weight of 130,000 was detected (lanes 1 and 2 in FIG. 7A), while from the cells infected with the two clones isolated from "BEDFH11", which is the recombinant virus constructed using plasmid "pEDFH11," a covalently cross-linked product of molecular weight of 50,000 was observed (lanes 3 and 4 in FIG. 7A). On the other hand, from the cells infected with the control virus constructed using the recombinant transfer vector, in which the DNA encoding EDF had been inserted in the opposite direction to the promoter, no covalently cross-linked product was detected. Lane 1 in FIG. 7B corresponds to the control virus-infected cells, lane 2 to the "BEDFH11"-infected cells, and lane 3 to the sample made by adding 214 fold non-labeled VEGF to the reaction in lane 2. Since the molecular weight of the VEGF$_{121}$ monomer is 20,000, it is subtracted from the molecular weights of the respective covalently cross-linked products to give 110,000 and 30,000. Therefore, it was inferred that the "BEDFH10"-infected cells produced the entire EDF, and that the "BEDFH11"-infected cells expressed a fragment of EDF. The fragment of EDF expressed by "BEDFH11" was designated as "EDFΔ11."

2) Affinity for VEGF

Figure 8A:
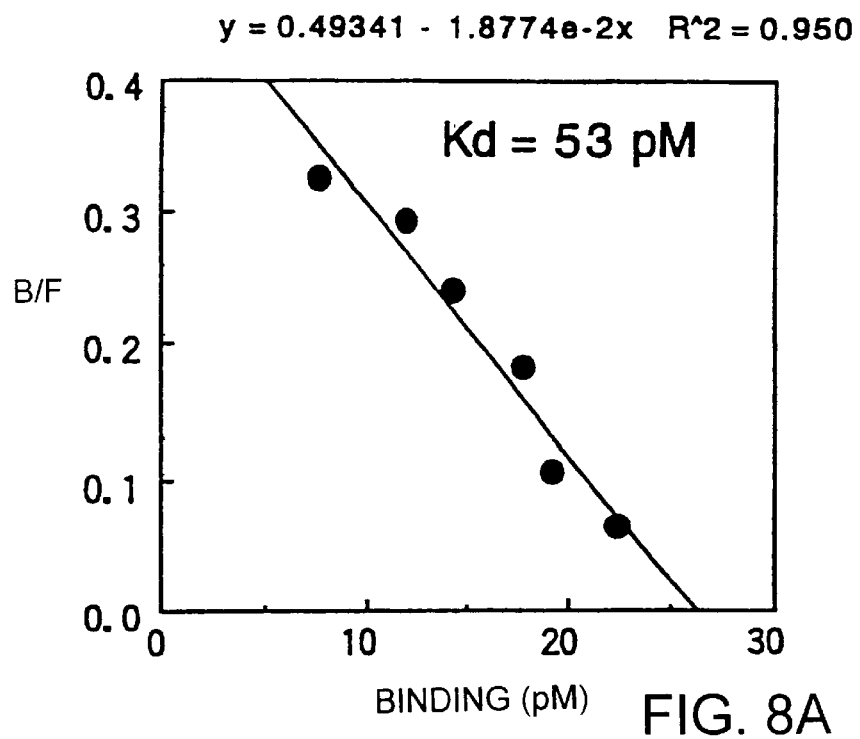
FIGS. 8A and 8B show the Scatchard analyses of the interactions between EDF or EDFΔ11 and the VEGF fragment.
Figure 8B:
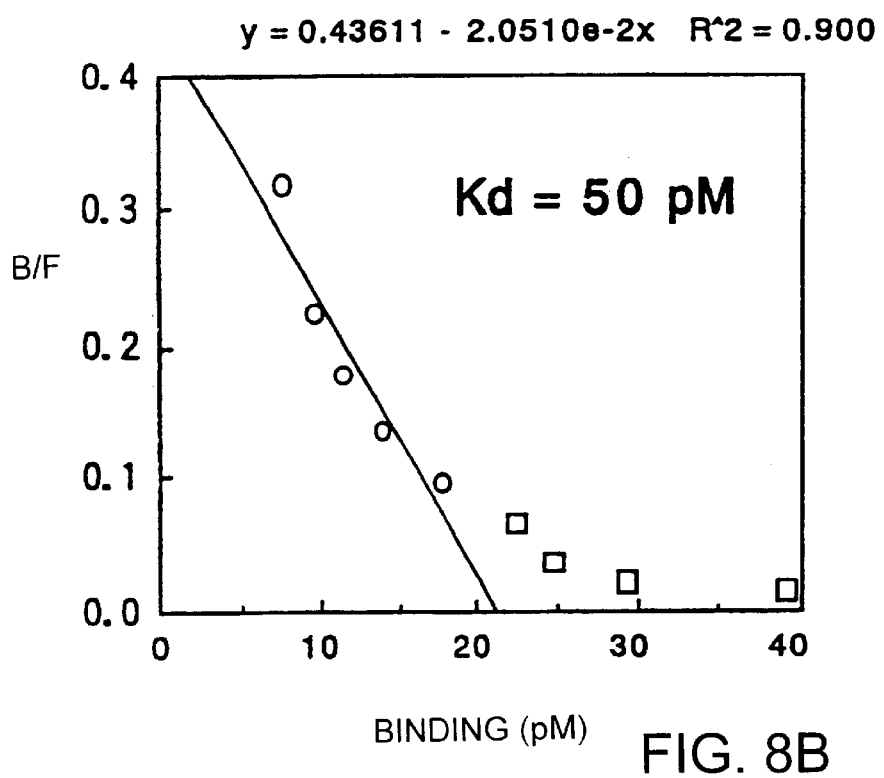

Sf9 cells were infected with the recombinant virus "BEDFH10" or "BEDFH11" at m.o.i. of 5 and 100 μl of the culture supernatants after 7 days of culturing were placed in the wells of microtiter plates (Immuron manufactured by Dynatech), followed by incubation at 4° C. overnight. The wells were emptied and washed 3 times with PBS-0.1% BSA. Then, 250 μl of PBS-1% BSA was added thereto and allowed to stand at room temperature for 2 hr for blocking. After the wells were emptied, 100 μl of a solution containing 11,300 cpm of $^{125}$I-VEGF$_{165}$ (manufactured by Amersham) having specific activity of 78,000 cpm/ng and 0–12,500 pg of unlabeled VEGF$_{125}$ was added thereto and allowed to stand at room temperature for 3 hr. The wells were emptied and washed 3 times with PBS-0. 1% BSA to measure the residual radioactivity in each well with a γ counter for Scatchard analysis (FIG. 8). FIGS. 8A and B show the results with the plates coated with EDF- and "EDFΔ11"-expressing culture supernatants, respectively. Since $^{125}$I-VEGF$_{165}$ was hardly bound to the plate coated with the culture supernatant of the control virus-infected Sf9 cells, the bound radioactivity can be considered to represent the binding of 125I-VEGF$_{165}$ to the inserted gene expressed products. The affinity of the expression products in the supernatants of "BEDFH10"- or "BEDFH11"-infected cells for VEGF$_{165}$ was Kd (dissociation constant)=about $5 \times 10^{-11}$", which was close to the values reported for FLT (J. Waltenberger et al., J. Biol. Chem., 269:26988 (1944)) or soluble FLT (R. L. Kendal and K. A. Thomas, Proc. Natl. Acad. Sci. U.S.A., 90:10705 (1993)).

3) Nucleotide sequence analysis of the insert DNAs in the recombinant transfer vector.

Nucleotide sequences were determined in order to confirm the cloned DNA's sequences in the plasmids "pEDFH10" and "pEDFH11" which revealed that the nucleotide sequence of the part of the insert DNA in "pEDFH10", which corresponds to the FLT extracellular domain, matched completely with that of FLT. The nucleotide sequence of the part of the insert DNA in "pEDFH11", which corresponds to the FLT extracellular domain, lacked the C at nucleotide position 1053 of SEQ ID NO:1, as compared with FLT. As a result, the open reading frame corresponded to residues-22 to 246 of the FLT amino acid sequence of SEQ ID NO:1. This portion contains the first and second domains of FLT.

4) Purification of the expression products.

Figure 9A:
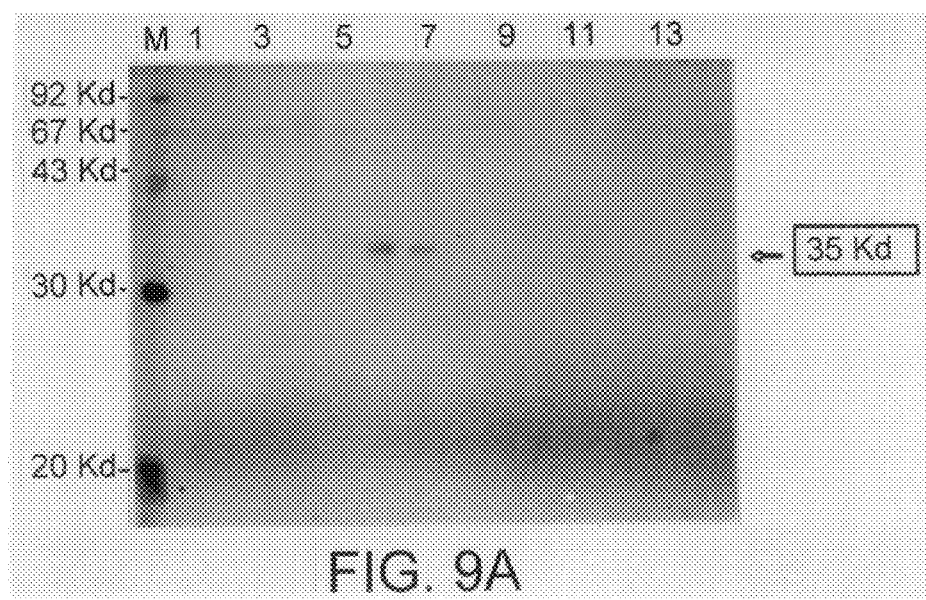
Figure 9B:
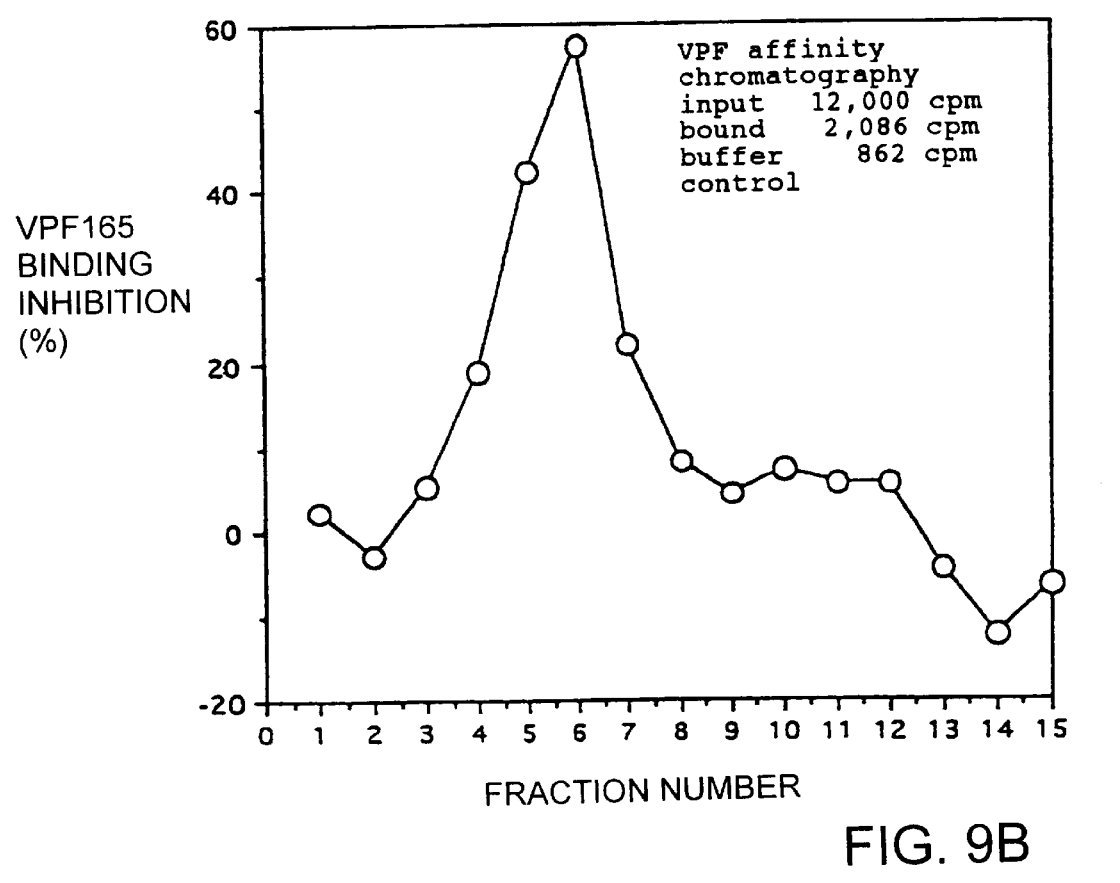

90 ml of Sf9 cells ($1.5 \times 10^6$/ml), which had been cultured at 27° C., 70 rpm in 100-ml Erlenmeyer flasks each containing TMN-FH 30 ml, were infected with "BEDFH10" or "BEDFH11" at m.o.i. 5. Twenty hr thereafter, the media were centrifuged to replace the media with 60 ml (30 ml×2) Ex-Cell 405 (manufactured by Iwaki Glass) and cultured for another 48 hr. 1/100 volume of phenylmethylsulfonyl fluoride/ethanol, 1/1000 volume of 100 μg/ml antipain, 200 μg/ml aprotinin, and 200 μg/ml leupeptin were added thereto and the supernatants were recovered. The culture supernatant of the "BEDFH10"-infected cells was concentrated 8-fold by "Immercible CX-10" (manufactured by Japan Millipore Ltd.). Ni$^{++}$-NTA (QIAGEN, Diagen GimbH) equilibrated with 20 mM Tris-HCl (pH 7.8)/50 mM KCl/0.1% Nonidet P-40/1 mM imidazole-HCl (pH 7.8) was added thereto and mixed at 4° C. for 1 hr. After centrifugation at 10,000 rpm, 30 ml of 150 mM KCl/0.1% Nonidet P-40/40 mM imidazole-HCl (pH 7.8) was added to the precipitate and mixed at 4° C. for 15 min. The precipitate was recovered by centrifugation and washed with the same buffer two more times. Then, 0.2 ml of 250 mM imidazole-HCl (pH 7.8) was added to the precipitate and mixed at room temperature for 15 min. The supernatant was recovered by centrifugation and 0.2 ml of 250 mM imidazole-HCl (pH 7.8) was again added to the precipitate. The supernatant was similarly recovered and combined with the previous one to serve as the purified EDF sample. NaCl was added to the culture supernatant of the "BEDFH11"-infected cells to a concentration of 0.3 M and fractionated by FPLC (Pharmacia Biosystem) using a heparin column (manufactured by Pharmacia Biosystem). After the sample was loaded, the column was washed with 0.1 M phosphate buffer (pH 7.0)—0.3 M NaCl until the absorbance at 280 nm became sufficiently low and eluted with a 0.3 M–1.0 M linear gradient of NaCl. The fractions absorbing at 280 nm were recovered and VEGF affinity chromatography was performed. The sample was diluted 2-fold with PBS, and loaded on 0.4 ml of the Sepharose 4B column coupled with 1.4 mg VEGF. The column was washed with 20 ml PBS-0.5 M NaCl, and eluted with 10 mM sodium acetate into the tube containing 0.05 ml 2M Tris-HCl (pH 8.0) at 0.5 ml/tube. Each fraction was subjected to SDS-polyacrylamide gel electrophoresis according to Laemmli, and silver-stained (FIG. 9A; lane numbers correspond to fraction numbers). Each fraction was also diluted 10 times with PBS-0.1% BSA, mixed with an equal volume of $^{125}$I-VEGF$_{165}$, and 1 hr thereafter, the VEGF binding was examined with 100 μl of the mixture using the microtiter plate used in Example 3-2). As a result, the fractions showing a band at the molecular weight of 35,000 by electrophoresis, which was almost in agreement with the value estimated from the results of the covalent cross-linking experiment, exhibited inhibition of VEGF binding (FIG. 9B).

5) Immunochemical analysis.

Figure 10A:
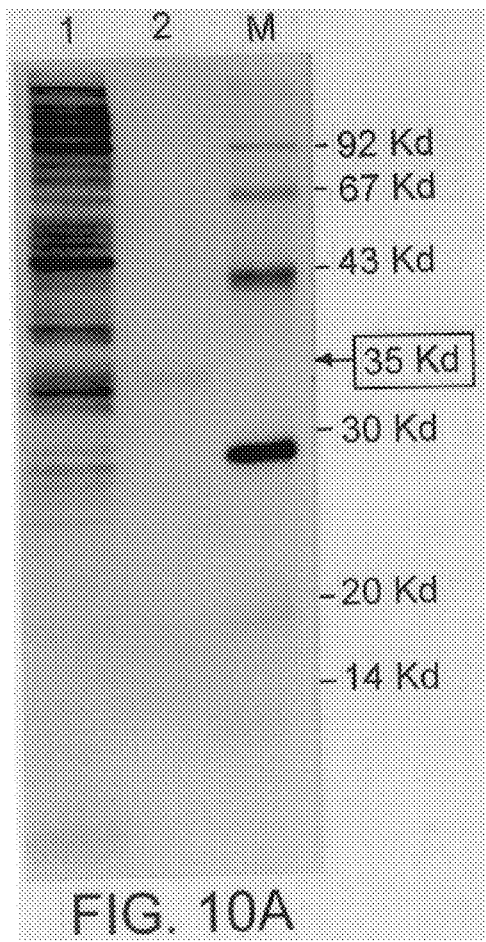
FIGS. 10A and 10B show the electrophoresis pattern and the western analysis of the purified EDFΔ11.
Figure 10B:
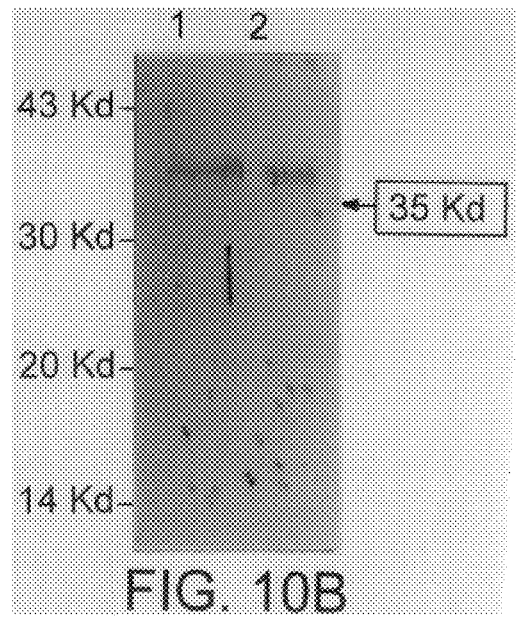

EDF or "EDF Δ 11" was subjected to SDS-polyacrylamide gel electrophoresis and western blotting was performed according to the method described in "Antibodies" by E. Harlow and D. Lane. The antibodies obtained in Example 1-4) were used at 2 μg/ml as the primary antibody, and a 5,000-fold diluted alkaline phosphatase-labeled anti-rabbit IgG (E. Y. Laboratories) as the secondary antibody to develop color by adding NTB (Nitroblue tetazolium chloride)/BCIP (5-bromo-4-chloro-3-indolylphosphate p-toluidine salt) (manufactured by Gibco BRL). As a result, a single band of about 35 kd was observed, which was confirmed to have specific reactivity with this antibody (FIG. 10B). From the above data, it was found that "EDFΔ11" corresponded to a polypeptide encompassing the N-terminal 267 amino acid residues of FLT. In FIG. 10A, lane 1 represents the sample after the heparin column and lane 2 after the VEGF affinity chromatography, both electrophoresed and silver-stained. FIG. 10B represents western blotting of the same samples.

6) Inhibition of the biological activities of VEGF.

Figure 6:
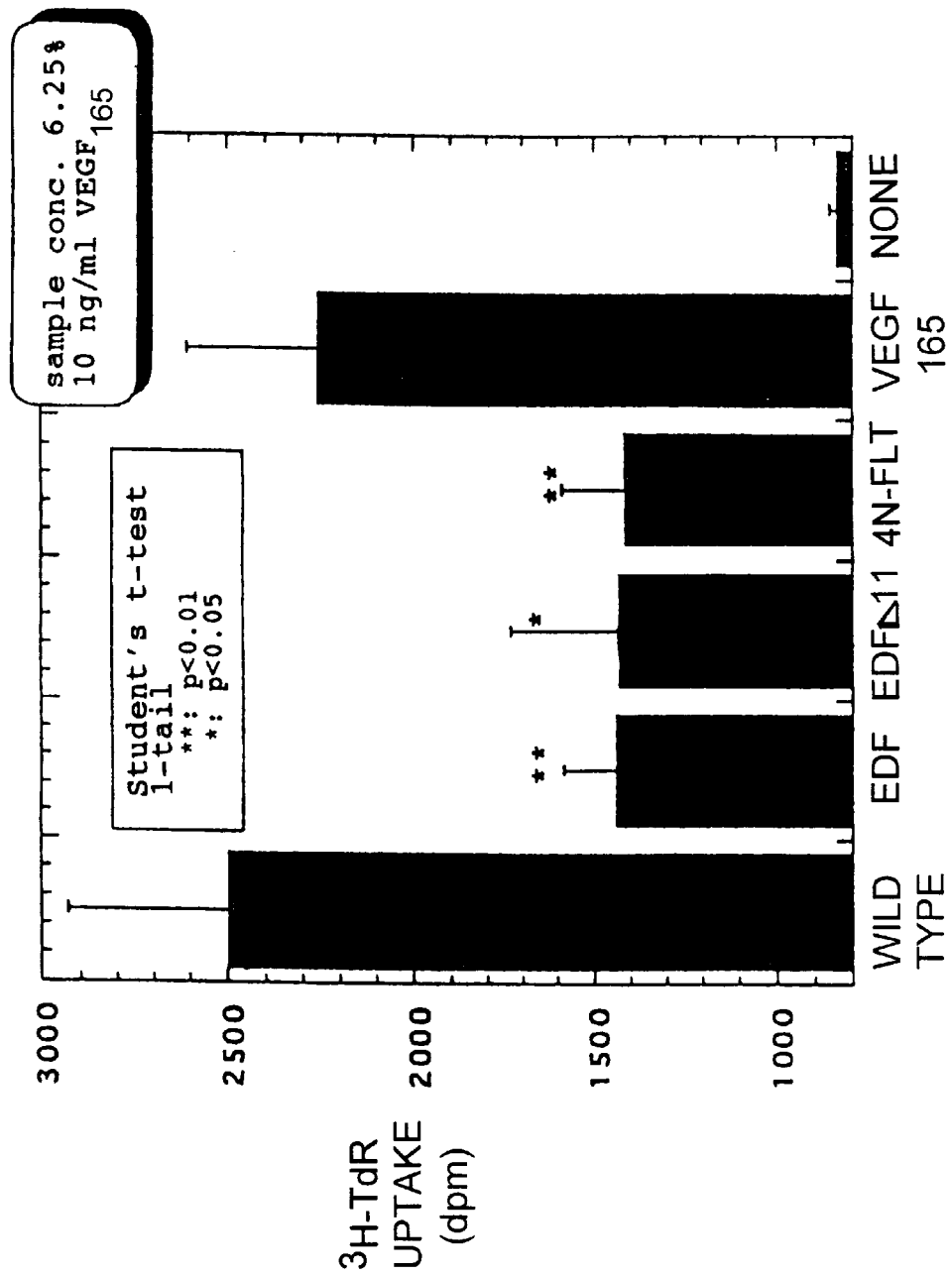
FIG. 6 shows the inhibition of the VEGF-dependent thymidine uptake in HUVEC by the culture supernatants of EDF-, 4N-FLT-, or EDF Δ11-expressing cells.

The "EDF"-expression culture supernatant, the "4N-FLT"-expression culture supernatant, and the "EDFΔ11"-expression culture supernatant were examined for inhibition of enhancement by VEGF of the thymidine uptake of the human umbilical cord-derived vascular endothelial cells (HUVEC). HUVEC cells (manufactured by Kurabo) were inoculated on a 96-well collagen plate (manufactured by Iwaki Glass) at 3,000 cells/well/100 μl (EGM-UV medium manufactured by Kurabo) and cultured at 37° C., 5% CO$_2$, for 24 hr. The cells were washed twice with PBS, 50 μl of 20 ng/ml VEGF$_{165}$ and 50 μl of the sample were added thereto followed by culturing for 4 days. Ten μl of 50 μCi/2 nmoles/ml of $^3$H-thymidine was added to each well and incubated for another 24 hr. After washing twice with PBS, the cells were detached by trypsin/EDTA and recovered on a glass filter by Cell Harvester (manufactured by Cambridge Technology, Inc.) to measure radioactivity with a scintillation counter (FIG. 6). Compared with the wild type virus-infected culture supernatant used as the control, the recombinant virus-derived "EDF," "4N-FLT," or "EDF Δ 11"-expression culture supernatant showed a significant inhibition of the VEGF-dependent thymidine uptake. The results elucidated that "EDF," "4N-FLT," or "EDFΔ11" inhibited enhancement by VEGF of the thymidine uptake by HUVEC, i.e., the enhancement of DNA synthesis.

III. Examples Concerning the Fusion Protein Between Globulin-like Domains 1 and 2 and the Human IgG$_1$-Fc Domain Example 8

1) Isolation of the human IgG$_1$-Fc cDNA.

When a IgG-producing cell line, human lymphoblastoma IM9 (Dainippon Pharmaceuticals), was cultured in the RPMI 1640 medium and the supernatant was examined using the Human IgG subclass profile kit (Zymed). As a result, the cell line was found to be producing human IgG$_1$. A cDNA solution was prepared from 4×10$^7$ IM9 cells by the same method as described in Example 5-1) of II. From this cDNA, the human IgG$_1$-Fc cDNA fragment was amplified in two steps of PCR using the conditions listed in Table 7 below.

TABLE 7

| Composition of the reaction mixture (in 100 μl) | PCR reaction condition |
| --- | --- |
| 10 μl LA-PCR buffer (Takara Shuzo) | 1) 95° C., 1 min; 1 cycle |
| 0.1 nM each dNTPS | 2) 94° C., 1 min; 56° C., 1 min; 72° C., 1 min; 20 cycles |
| 2 μl cDNA solution | 3) After adding 200 μM each of primers 9 and 10; 94° C., 1 min; 56° C., 1 min; 72° C., 1 min; 15 cycles |
| 200 nM primer 7 | |
| 200 nM primer 8 | |
| 5.0 U ExTaq polymerase (Takara Shuzo) | 4) 72° C., 7 min; 1 cycle |

The sequences of the primers used in the above reaction were as follows:

```
Primer 7:  5'-TCTTGTGACAAAACTCACACATGC-3'           (SEQ ID
                                                    NO:14)

Primer 8:  5'-CGGAGACAGGGAGAGGCTCTTCTG-3'           (SEQ ID
                                                    NO:15)

Primer 9:  5'-GAGCCCAAATCTTGTGACAAAA-3'             (SEQ ID
                                                    NO:16)

Primer 10: 5'-TTCTCGGATCCTTATTTACCCGGAGACAGGGA-3'   (SEQ ID
                                                    NO:17)
              Bam  STP  hIgG1-Fc term
```

Figure 1:
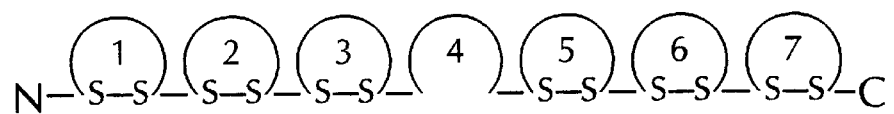
Figure 11:
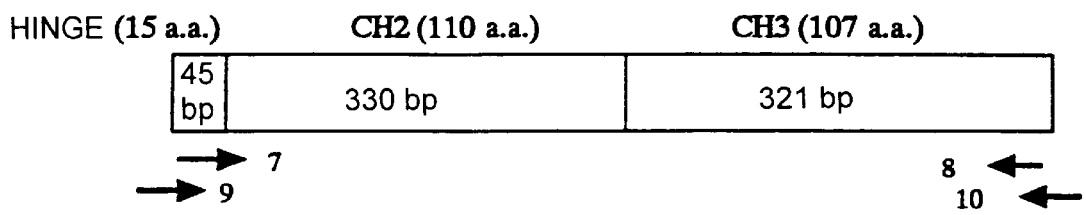
FIG. 11 shows a schematic diagram of the Fc domain of human immunoglobulin $IgG_1$ and the relative positions of the primers used for isolating fragments.

Concerning Primer 10, "Bam" indicates the restriction enzyme BamHI recognition site, "STP" the stop codon, and "hIgG1-Fc term" a C-terminal portion of the human IgG$_1$-Fc coding region. Note that Primer 8 and Primer 10 are antisense strands. The relationships between the human IgG$_1$-Fc coding region and the positions of the primers are shown in FIG. 11. The PCR reaction mixture was treated as in Example 5-2) of II and subjected to agarose gel electrophoresis. A DNA fragment of approximately 700 bp was excised and the DNA was recovered by centrifugation in a SUPEREC-01 filter tube (Takara Shuzo). The restriction enzyme digestion patterns of this DNA fragment with AvaI, HpaII, RsaI, and SmaI (Table 8) were examined, and it was confirmed that they matched with those derived from the reported human IgG$_1$-Fc cDNA sequence (J. W. Ellison, B. J. Berson and L. E. Hood, Nucleic Acid Res., 10: 4071 (1982)).

TABLE 8

| Sizes of the generated DNA fragments (bp) | |
|---|---|
| Intact | 700 |
| AvaI | 380, 280 |
| HpaII | 300, 190, 110, 110 |
| RsaI | 300, 200, 75, 75 |
| SmaI | 480, 280 |

Example 9

Construction of the expression system for the fusion protein between immunoglobulin-like domains 1 and 2 and the human IgG$_1$-Fc domain 1) Isolation of the signal peptide encoding DNA of *E. coli* outer membrane protein Omp A.

The HB101 strain of *E. coli* was cultured in 2×TY medium at 37° C., overnight, and the cell body was recovered by centrifugation and resuspended in 0.5 ml TE buffer (10 mM Tris-HCl (pH 7.5)/1 mM EDTA). After lysis by adding 25 µl of 20 mg/ml egg white lysozyme and incubating at room temperature for 15 min, 50 µl of 10% SDS and 0.5 ml TE-saturated phenol were added thereto and vigorously shaken for 5 min. The aqueous layer was recovered by centrifugation and treated with an equal volume of chloroform to remove the phenol. The DNA was precipitated by adding a double volume of ethanol and washed with 70% ethanol followed by drying. The resulting precipitate was dissolved in 200 µl of 20 µg/ml RNase A solution to prepare an *E. coli* genome DNA solution. This was used as the template to perform PCR according to the conditions given in Table 9 to provide an amplified Omp A signal peptide encoding DNA.

TABLE 9

| Composition of the reaction mixture (in 100 µl) | PCR reaction condition |
|---|---|
| 10 µl LA-PCR buffer (Takara Shuzo) | 1) 95° C., 1 min; 1 cycle |
| 0.1 mM each dNTPS | 2) 94° C., 1 min; 56° C., 1 min; 72° C., 1 min; 35 cycles |
| 2 µl *E. coli* genome DNA | 3) 72° C., 7 min; 1 cycle |
| 200 nM primer 11 | |
| 200 nM primer 12 | |
| 5.0 U ExTaq polymerase (Takara Shuzo) | |

The sequences of the primers used in the above reaction were as follows:

```
Primer 11:
    5'-TAACCTGGCGATAACGAGGCGCAAATAATGAAAAAG-3'  (SEQ ID
                                                NO:18)
       trx term      SD          omp init Primer 12
    5'-CTGAACTAGATTTCGGAGCGGCCTGCGCTA-3'        (SEQ ID
                                                NO:19)
         mflt        omp SP term
```

Figure 12:
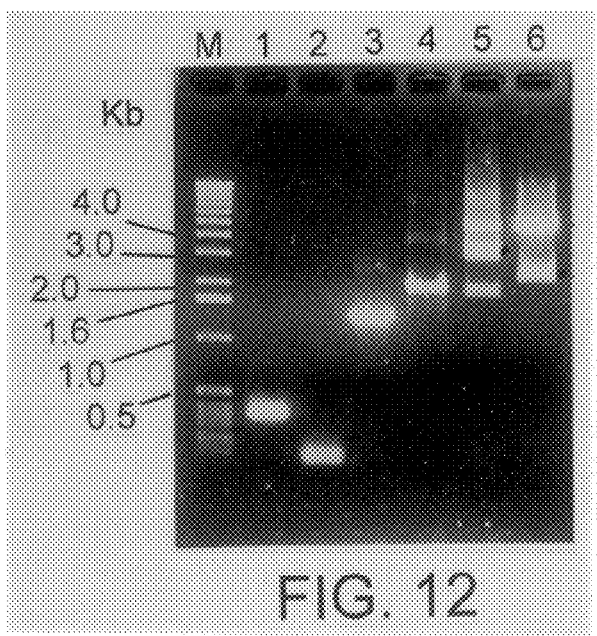
FIG. 12 shows the agarose gel electrophoresis patterns of the PCR-amplified and purified DNA and the recombinant plasmid digested with restriction enzymes.

Concerning Primer 11, "trx term" indicates the terminal coding sequence of the *E. coli* thioredoxin gene (trx A), "SD" the ribosome binding sequence of omp A, and "omp init" the vicinity of the initiation codon-containing sequence of omp A. Concerning Primer 12, "mflt" indicates the N-terminal coding region of the mature FLT, and "omp SP term" the terminal portion of the Omp A signal peptide coding region. Note that Primer 12 is an antisense strand. The sequence of the thioredoxin gene was based on "B. J. Wallace and S. R. Kushner, Gene 32: 399 (1984)" and that for the omp A gene was based on "E. Beck and E. Bremmer, Nucleic Acid Res., 8: 3011 (1980)". The PCR reaction mixture was treated as described above, and the DNA fragment thus obtained was used as the omp A signal peptide DNA (FIGS. 12 and 14).

2) Amplification and isolation of the *E. coli* thioredoxin gene.

As mentioned before, when an exogenous protein is expressed at a high level, it tends to form insoluble inclusion bodies. Denaturation, solubilization, and reactivation of the inclusion bodies make recovery low and requires labor. Under these circumstances it has been reported that a simultaneous high level expression of *E. coil* thioredoxin intracellularly may allow the exogenous protein to fold correctly, thereby reducing the possibility of the inclusion body formation (T. Yasukawa et al., J. Biol. Chem. 270: 25328 (1995)). Therefore, in order to express thioredoxin at a high level, the gene was isolated.

Using the conditions listed below, PCR was performed and the *E. coli* thioredoxin gene was amplified.

TABLE 10

| Composition of the reaction mixture (in 100 µl) | PCR reaction condition |
|---|---|
| 10 µl LA-PCR buffer (Takara Shuzo) | 1) 95° C., 1 min; 1 cycle |
| 0.1 mM each dNTPs | 2) 94° C., 1 min; 56° C., 1 min; 72° C., 1 min; 35 cycles |
| 2 µl *E. coli* genome DNA | 3) 72° C., 7 min; 1 cycle |
| 200 nM primer 13 | |
| 200 nM primer 14 | |
| 5.0 U ExTaq polymerase (Takara Shuzo) | |

The sequences of the primers used in the above reaction were as follows:

```
Primer 13: 5'-TTCTCGAATTCCCTGTGGAGTTATATATGAGC-3' (SEQ ID
                                                   NO:20)
```

```
                               -continued
                  Eco         SD          trx init
Primer 14: 5'-GCCTCGTTATCGCCAGGTTAGCGTCGAGGA-3'    (SEQ ID
                                                    NO:21)
              omp SD           trx term
```

Concerning Primer 13, "Eco" indicates the restriction enzyme EcoRI recognition site, "SD" the ribosome binding sequence of the *E. coli* thioredoxin gene, and "trx init" the vicinity of the initiation codon-containing sequence of trx A. Concerning Primer 14, "omp SD" indicates the ribosome binding sequence of omp A. Note that Primer 14 is an antisense strand. The PCR reaction mixture was treated as described above, and the DNA fragment thus obtained was used as the thioredoxin DNA (FIGS. 12 and 14).

3) The fusion between the DNA encoding the immunoglobulin-like domains 1 and 2 of FLT and the DNA encoding the human IgG$_1$-Fc domain.

Using EDFΔ11-expressing baculovirus vector, pEDFH11, as the template, PCR was performed under the conditions listed in Table 11, to amplify the DNA encoding the immunoglobulin-like domains 1 and 2 of FLT. The reaction mixture was purified as described above, and used as the EDF12 DNA (FIG. 13).

TABLE 11

| Composition of the reaction mixture (in 100 μl) | PCR reaction condition |
| --- | --- |
| 10 μl LA-PCR buffer (Takara Shuzo) | 1) 95° C., 1 min; 1 cycle |
| 0.1 mM each dNTPs | 2) 94° C., 1 min; 56° C., 1 min; 72° C., 1 min; 20 cycles |
| 0.8 μg pEDFH10 DNA | 3) 72° C., 7 min; 1 cycle |
| 200 nM primer 15 | |
| 200 nM primer 16 | |
| 5.0 U ExTaq polymerase (Takara Shuzo) | |

The sequences of the primers used in the above reaction were follows:

```
Primer 15:
  5'-CGCTCCGAAA TCTAGTTCAGGTTCAAAATT-3'              (SEQ ID
                                                     NO:22)
     omp SP term          mFLT Primer 16:
  5'-TTTgTCACAAgATTTgggCTCT gTgCTTATTTggACATCTAT-3'  (SEQ ID
                                                     NO:23)
       hIgG-Fc hinge              214-FLT-208
```

Concerning Primer 16, "hIgG-Fc hinge" indicates the human IgG$_1$ hinge encoding DNA, and "214-FLT-208" the DNA encoding amino acid residues 208 through 214 of FLT. Note that Primer 16 is an antisense strand.

Using the DNA encoding the immunoglobulin-like domains 1 and 2 of FLT (EDF12 DNA) thus obtained and the IgG$_1$-Fc cDNA obtained in Example 8-1) as the template, a recombinant PCR (R. Higuchi, in "PCR Protocols," ed. by M. A. Innis et al., Academic Press Inc. (1990)) was performed under the conditions listed in Table 12 to fuse and amplify the two DNA fragments. The reaction mixture was purified as described above, and used as the EDF12Fc DNA (FIGS. 13 and 14).

TABLE 12

| Composition of the reaction mixture (in 100 μl) | PCR reaction condition |
| --- | --- |
| 10 μl LA-PCR buffer (Takara Shuzo) | 1) 95° C., 1 min; 1 cycle |
| 0.1 mM each dNTPS | 2) 94° C., 1 min; 56° C., 1 min; 72° C., 1 min; 25 cycles |
| 0.1 μg EDF12 DNA | 3) 72° C., 7 min; 1 cycle |
| 0.1 μg hIgG Fc cDNA | |
| 200 nM primer 15 | |
| 200 nM primer 10 | |
| 5.0 U ExTaq polymerase (Takara Shuzo) | |

4) Construction of the expression vector.

Figure 13:
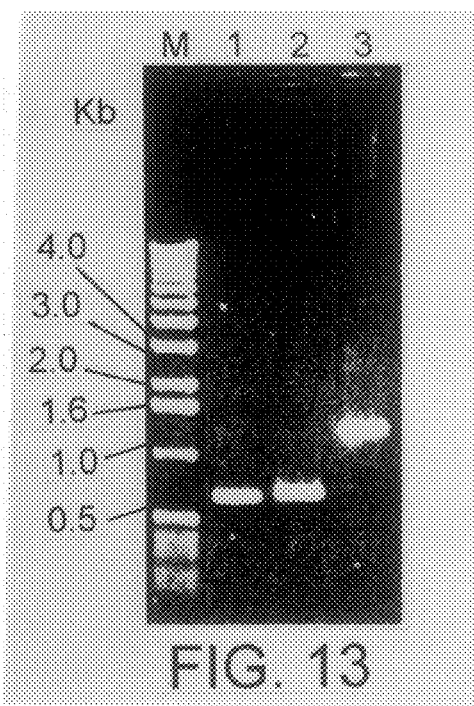
FIG. 13 shows the agarose gel electrophoresis patterns of the PCR-amplified and purified DNA.

Using the omp A signal peptide encoding DNA of Example 9-1), the thioredoxin DNA of Example 9-2), the EDF12Fc DNA of Example 9-3) as the template, a recombinant PCR was performed under the conditions listed in Table 13 to fuse and amplify the three DNA fragments, and the reaction mixture was purified (FIGS. 13 and 14). In FIG. 13, lanes M, 1, 2, and 3 represent the molecular weight standard, EDF12 DNA, IgG$_1$-Fc DNA, and EDF12Fc DNA, respectively. In FIG. 14, "Ec" and "Bm" indicate the restriction enzyme EcoRI and BamHI recognition sites, respectively.

TABLE 13

| Composition of the reaction mixture (in 100 μl) | PCR reaction condition |
| --- | --- |
| 10 μl LA-PCR buffer (Takara Shuzo) | 1) 95° C., 1 min; 1 cycle |
| 0.1 mM each dNTPS | 2) 95° C., 1 min; lowering temperature to 55° C. over 15 |

TABLE 13-continued

| Composition of the reaction mixture (in 100 μl) | PCR reaction condition |
| --- | --- |
| 0.1 μg Omp A signal peptide DNA | min; 55° C., 2 min; 72° C., 2.5 min; 3 cycles |
| 0.1 μg thioredoxin DNA | |
| 0.1 μg EDF12FcDNA | 3) 94° C., 1 min; 56° C., 1 min; 72° C., 2.5 min; 22 cycles |
| 200 nM primer 13 | |
| 200 nM primer 10 | 4) 72° C., 7 min; 1 cycle |
| 5.0 U ExTaq polymerase (Takara Shuzo) | |

The approximately 1.7 kbp DNA fragment thus obtained had an EcoRI and a BamHI restriction sequence, which was contained in Primer 10 or Primer 13, on either end. This 1.7 kbp fusion DNA fragment was digested with EcoRI and BamHI. Separately, an *E. coli* expression vector pTTQ18 (manufactured by Amersham Japan) was digested with EcoRI and BamHI. These restriction enzyme digestion reaction mixtures were treated as in Example 5-2) to recover the DNAs. Using the Ligation Kit (Takara Shuzo), the ligation reaction was done at a vector: insert ratio of 3:1. Using this ligation mixture and *E. coli* JM109 competent cells (manufactured by Takara Shuzo), the transformation was performed and the transformants viable on an agar medium containing ampicillin were selected. From these transformants, using the same method as in Example 5-2), several recombinant clones containing the 1.7 kbp insert DNA were obtained, one of which was named JM109 (pEDF12Fc).

In FIG. 12, lanes M, 1, 2, 3, 4, 5, and 6 represent the molecular weight standard, thioredoxin DNA, Omp A signal peptide DNA, EDF12Fc DNA, thioredoxin DNA-Omp A signal peptide DNA-EDF12Fc DNA fusion fragment, pEDF12Fc DNA digested with EcoRI+BamHI, and pTTQ18 DNA digested with EcoRI+BamHI. (Undigested plasmids are indicated by the circle.)

Example 10

Analysis of the Expressed Fusion Protein

1) Preparation of the crude extract.

JM109 (pEDF12Fc) was shake-cultured at 37° C. in 70 ml of 2×TY medium containing 100 μg/ml ampicillin, IPTG was added to 0.5 mM when the absorbance at 600 nm reached 1.0, and the medium was cultured for another 12 hr. After completion of the culturing, the culture medium was rapidly chilled, 70 μl of 33 μM pAPMSF (Wako Pure Chemical Industries) was added as a protease inhibitor followed by centrifugation to recover the bacterial cells. The cells were resuspended in 5 ml of 10 mM Tris-HCl (pH 8.0)/33 nM pAPMSF, and more than 95% of the cells were disrupted by ultrasonication. The suspension was centrifuged at 10,000 g for 20 min, the precipitate was dissolved in 5 ml of 0.1 M Tris-HCl (pH 8.0)/1 M KCl/33 nM pAPMSF/5 mM EDTA/1% Triton X100/0.1% Nonidet-P40, centrifuged at 20,000 g to remove the insoluble matters, and the supernatant was used in the following analyses as a crude extract. At the same time, a crude extract derived from JM109 (pTTQ18) containing only the vector portion, was similarly prepared as a control.

2) Confirmation of the fusion protein expression by EIA.

Expression was confirmed by a sandwich EIA using VEGF and an anti-human IgG antibody. In order to prepare the VEGF-coated plate, VEGF$_{165}$ (manufactured by R&D) was diluted to 50 ng/ml with PBS and aliquoted at 100 μl/well on an Immuron 2 microtiter plate. After allowing to stand at 4° C. overnight, the plate was blocked as in Example 7-2). JM109 (pTTQ18) and JM109 (pEDF12Fc) crude extracts were diluted 20-fold with PBS/0.1% BSA and aliquoted at 100 μl/well. The plate was allowed to stand at room temperature for 1 hr and the wells were washed 6 times with PBS/0.1% BSA. Next, 100 μl of the peroxidase-labeled anti-human IgG antibody (#IM-0837 manufactured by MBL), diluted 1,000-fold with PBS/0.1% BSA, was added to each well allowed to stand at room temperature for 1 hr, followed by washing the well 6 times as described above. One hundred μl of the peroxidase substrate solution (20 mM sodium acetate (pH 5.2), 0.01% hydrogen peroxide, orthophenylene diamine tablet (manufactured by Wako Pure Chemical Industries) 1 tablet/20 ml) were then added to the well, the color reaction was allowed to proceed at room temperature for 30 min, the reaction was stopped by adding 100 μl of 2 N sulfuric acid, and the absorbance at 492 nm was measured. As a result, it was found that the recombinant JM109 (pEDF12Fc) extract developed more intense color than the control (Table 14). Since the experiment was a sandwich EIA using VEGF and an anti-human IgG antibody, the results suggested that the recombinant extract contained molecules which bound to VEGF as well as the anti-human IgG antibody.

TABLE 14

| 20-fold dilution of crude extract | JM109 (pTTQ18) | JM109 (pEDF12Fc) |
|---|---|---|
| absorbance (492 nm) | 0.118 | 1.056 |

3) Confirmation of the molecular weight of the recombinant protein.

In order to examine the molecular weight of the recombinant protein, the crude extract was subjected to western blot analysis using the method as in Example 7-5). The crude extract was electrophoresed on an SDS-polyacrylamide gel according to Laemmli and electroblotted onto a PDVF membrane. After blocking, 0.4 μg/ml of an anti-human IgG$_1$-Fc monoclonal antibody (MBL #IM-0280) was used as the primary antibody and a 4,000-fold diluted alkaline phosphatase-labeled anti-mouse IgG (Zymed) was used as the secondary antibody. As a result, only on the lane with the JM109 (pEDF12Fc) crude extract, an immunochemically reactive band at the molecular weight of about 60,000 under the reducing condition, was detected (FIG. 15). In FIG. 15, the samples on lanes 1 and 2 were the JM109 (pTTQ18) crude extract and the JM109 (pEDF12Fc) crude extract, respectively. Since the expected recombinant protein consists of 446 amino acid residues, the size of the observed band was reasonable.

4) Analysis of the covalently cross-linked products with $^{125}$I-VEGF$_{165}$.

In order to examine the molecular weight of the bound complex between the recombinant protein and VEGF, 100 μl each of the crude extracts and 140,000 cpm of $^{125}$I-VEGF$_{165}$ were mixed. After a 2-hr room temperature incubation, immunoprecipitation was performed according to the method described in "Molecular Cloning" by Sambrook et al. using protein A-Sepharose (manufactured by Pharmacia) and the cross-linking reaction was done using the same method as in Example 7-1). The precipitates were subjected to SDS-polyacrylamide gel electrophoresis and the signal was detected by autoradiography (FIG. 16). As a result, while only a weak VEGF signal was detected from the control extract (lane 2), the recombinant JM109 (pEDF12Fc) extract (lane 1) gave a cross-linked product having a molecular weight of about 1,520,000 under the reducing condition. The results indicated that the recombinant protein bound to VEGF to produce a stable complex, and that it also bound to protein A.

5) Measurement of the affinity of the recombinant protein for VEGF.

In order to know the binding affinity of the recombinant protein for VEGF, Scatchard analysis (N=3) was done as in Example 7-2) (FIG. 17). Twenty μg/ml of protein A (KPL) was coated at 150 μl/well on an Immuron 2 plate, and after blocking, the crude extract was added thereto at 150 μl/well. After allowing to stand at room temperature for 1 hr, the plate was washed 3 times with PBS/0.1% BSA/1 mM EDTA/0.25% gelatin/0.1% Nonidet-P40. The same buffer was used when $^{125}$I-VEGF$_{165}$ was washed. The results indicated that the recombinant protein possesses affinity for VEGF comparable to EDF.

6) Inhibition of VEGF's biological activities by the recombinant protein.

In order to partially purify the recombinant protein of the present invention, protein A-Sepharose column chromatography was performed, and the protein was eluted at pH 4.0. BSA was added to the elution to 1 mg/ml and dialyzed against PBS to subject the resulting sample to the following experiments. The other samples were also dialyzed after an addition of BSA.

As in Example 7-6), the recombinant protein of the present invention was examined for inhibitory activity against the VEGF-dependent enhancement of the $^3$H-thymidine uptake of HUVEC. Four μg/ml of human IgG$_1$ was used as a negative control and 2 μg/ml of purified EDF was used as a positive control. When the recombinant protein, which was partially purified by protein A-Sepharose, was used at 1 μg/ml, a notable VEGF inhibitory activity was observed as with EDF (FIG. 18). On the other hand, the addition of human IgG$_1$ did not result in such inhibition. From these results, it was demonstrated that the recombinant protein of the present invention could inhibit the vascular endothelial cell proliferation enhancement activity of VEGF.

The above results indicated that the recombinant protein of the present invention, the FLT immunoglobulin-like domains 1 and 2-human IgG$_1$-Fc domain fusion protein, had such biochemical characteristics of human IgG$_1$-Fc as being recognized by the human IgG$_1$-Fc-specific monoclonal antibody and as binding to protein A. Furthermore, it was demonstrated that the fusion protein of the present invention bound to VEGF with high affinity comparable to EDF and that it also inhibited the biological activity of VEGF.

INDUSTRIAL APPLICABILITY

The polypeptides of the present invention can be utilized in treating diseases accompanying pathological neovascularization, such as solid tumors, because they can inhibit the VEGF-stimulated neovascularization. In addition, since they are constituted by human-derived amino acids, they are unlikely to trigger antibody production even if they are administered for a prolonged period of time. Furthermore, since they have smaller molecular weights than the conventional polypeptides (R. L. Kendal and K. A. Thomas, Proc. Natl. Acad. Sci. U.S.A., 90:10705 (1993)), it is easier to express them using recombinant DNA techniques, and they infiltrate into diseased sites more quickly.

What is claimed is:

1. A DNA encoding a polypeptide consisting of immunoglobulin-like domains 1 and 2 of FLT-1, and optionally (a) a portion of immunoglobulin-like domain 3 of FLT-1, (b) a signal sequence of FLT-1, or (c) a portion of immunoglobulin-like domain 3 of FLT-1 and the signal sequence of FLT-1, said polypeptide being capable of inhibiting an activity of vascular endothelial call growth factor (VEGF) by binding to VEGF.

2. The DNA of claim 1, wherein the polypeptide comprises amino acid residues 1 to 208 of SEQ ID NO: 24.

3. A vector comprising the DNA of claim 1.

4. A transformant comprising the DNA of claim 1.

5. A method of producing a polypeptide, comprising culturing the transformant of claim 4 under conditions appropriate for expressing the DNA and recovering the polypetide from the culture of the transformant, thereby producing the polypeptide.

6. The DNA of claim 1, wherein the polypeptide consists of immunoglobulin-like domain 1 and immunoglobulin-like domain 2 of FLT-1.

7. The DNA of claim 1, wherein the polypeptide consists of immunoglobulin-like domain 1, immunoglobulin-like domain 2 and a portion of immunoglobulin-like domain 3 of FLT-1.

8. The DNA of claim 1, wherein the polypeptide consists of the signal sequence, immunoglobulin-like domain 1, and immunoglobulin-like domain 2 of FLT-1.

9. The DNA of claim 1, wherein the polypeptide consists of the signal sequence, immunoglobulin-like domain 1, immunoglobulin-like domain 2, and a portion of immunoglobulin-like domain 3 of FLT-1.

10. A DNA encoding a polypeptide consisting of immunoglobulin-like domain 1, immunoglobulin-like domain 2 and a portion of immunoglobulin-like domain 3 of SEQ ID NO: 24, said polypeptide being capable of inhibiting an activity of VEGF by binding to VEGF.

11. A DNA encoding a polypeptide consisting of a signal sequence, immunoglobulin-like domain 1, immunoglobulin-like domain 2, and a portion of immunoglobulin-like domain 3 of SEQ ID NO:24, said polypeptide being capable of inhibiting an activity of VEGF by binding to VEGF.

* * * * *

UNITED STATES PATENT AND TRADEMARK OFFICE
CERTIFICATE OF CORRECTION

PATENT NO.        : 6,270,993 B1
APPLICATION NO. : 09/051363
DATED             : August 7, 2001
INVENTOR(S)       : Masabumi Shibuya et al.

It is certified that error appears in the above-identified patent and that said Letters Patent is hereby corrected as shown below:

Title page, Item (56),
Foreign Patent Doument WO 95/33050, replace "7/1995" with -- 12/1995 --

Title page, Item (56),
"M. Shibuya et al.," replace "(fit)" with -- (flt) --

Title page, Item (57) Abstract,
Line 6, replace "main" with -- domain --

Drawings, Delete Fig. 2, and replace with Fig. 2, as shown below,

--                                                                                             --

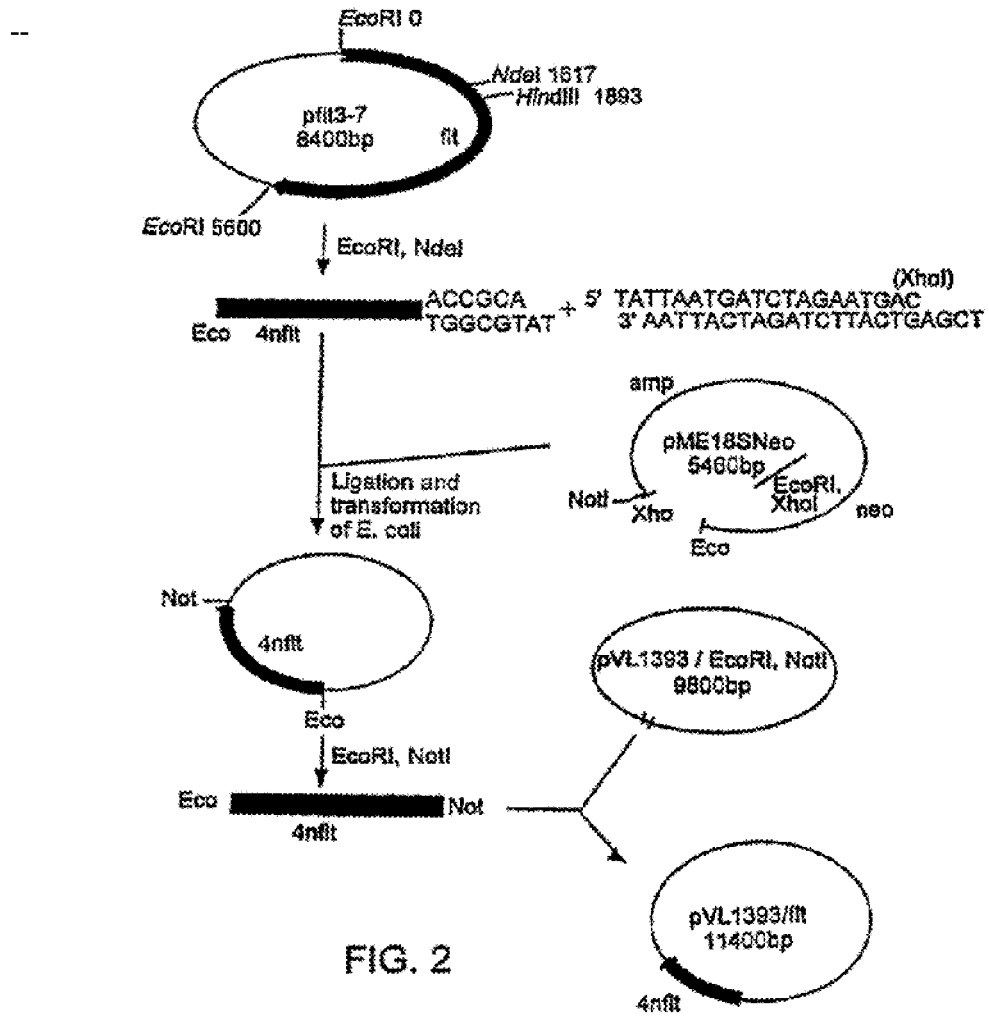

FIG. 2

UNITED STATES PATENT AND TRADEMARK OFFICE
CERTIFICATE OF CORRECTION

PATENT NO. : 6,270,993 B1  
APPLICATION NO. : 09/051363  
DATED : August 7, 2001  
INVENTOR(S) : Masabumi Shibuya et al.

It is certified that error appears in the above-identified patent and that said Letters Patent is hereby corrected as shown below:

Drawings, Delete Fig. 3 and replace with Fig. 3, as shown below,

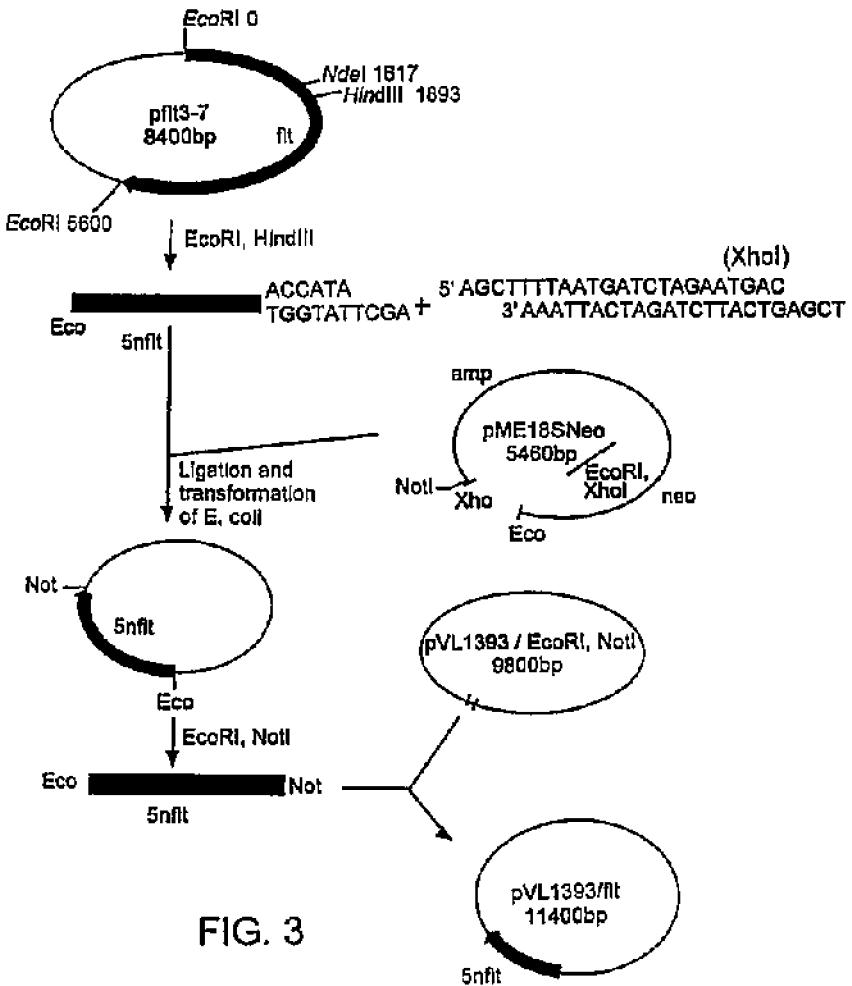

FIG. 3

UNITED STATES PATENT AND TRADEMARK OFFICE
CERTIFICATE OF CORRECTION

PATENT NO.       : 6,270,993 B1
APPLICATION NO.  : 09/051363
DATED            : August 7, 2001
INVENTOR(S)      : Masabumi Shibuya et al.

It is certified that error appears in the above-identified patent and that said Letters Patent is hereby corrected as shown below:

Drawings, Delete Fig. 6, and replace with Fig. 6, as shown below,

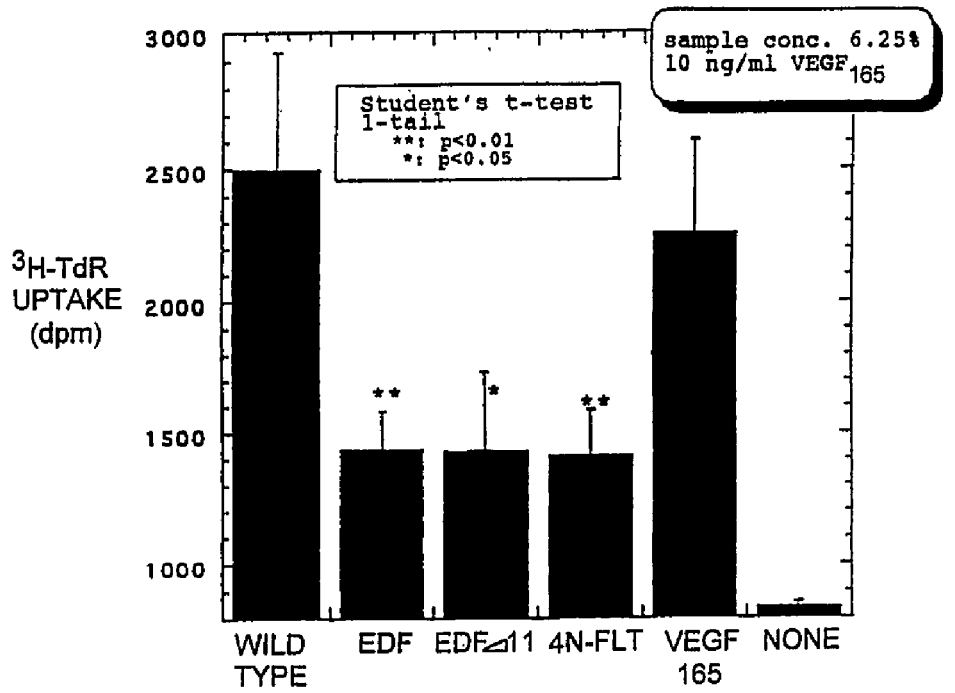

FIG. 6

UNITED STATES PATENT AND TRADEMARK OFFICE
CERTIFICATE OF CORRECTION

PATENT NO. : 6,270,993 B1
APPLICATION NO. : 09/051363
DATED : August 7, 2001
INVENTOR(S) : Masabumi Shibuya et al.

It is certified that error appears in the above-identified patent and that said Letters Patent is hereby corrected as shown below:

Drawings, Delete Fig. 13, and replace with Fig. 13, as shown below,

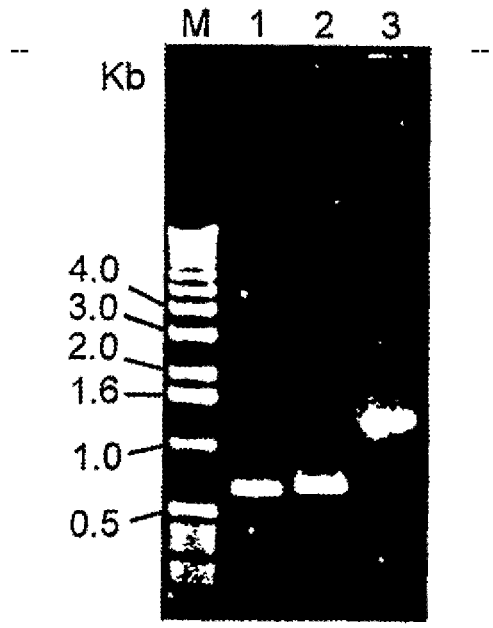

FIG. 13

UNITED STATES PATENT AND TRADEMARK OFFICE
CERTIFICATE OF CORRECTION

PATENT NO.        : 6,270,993 B1
APPLICATION NO.   : 09/051363
DATED             : August 7, 2001
INVENTOR(S)       : Masabumi Shibuya et al.

It is certified that error appears in the above-identified patent and that said Letters Patent is hereby corrected as shown below:

Drawings, Delete Fig. 14, and replace with Fig. 14, as shown below,

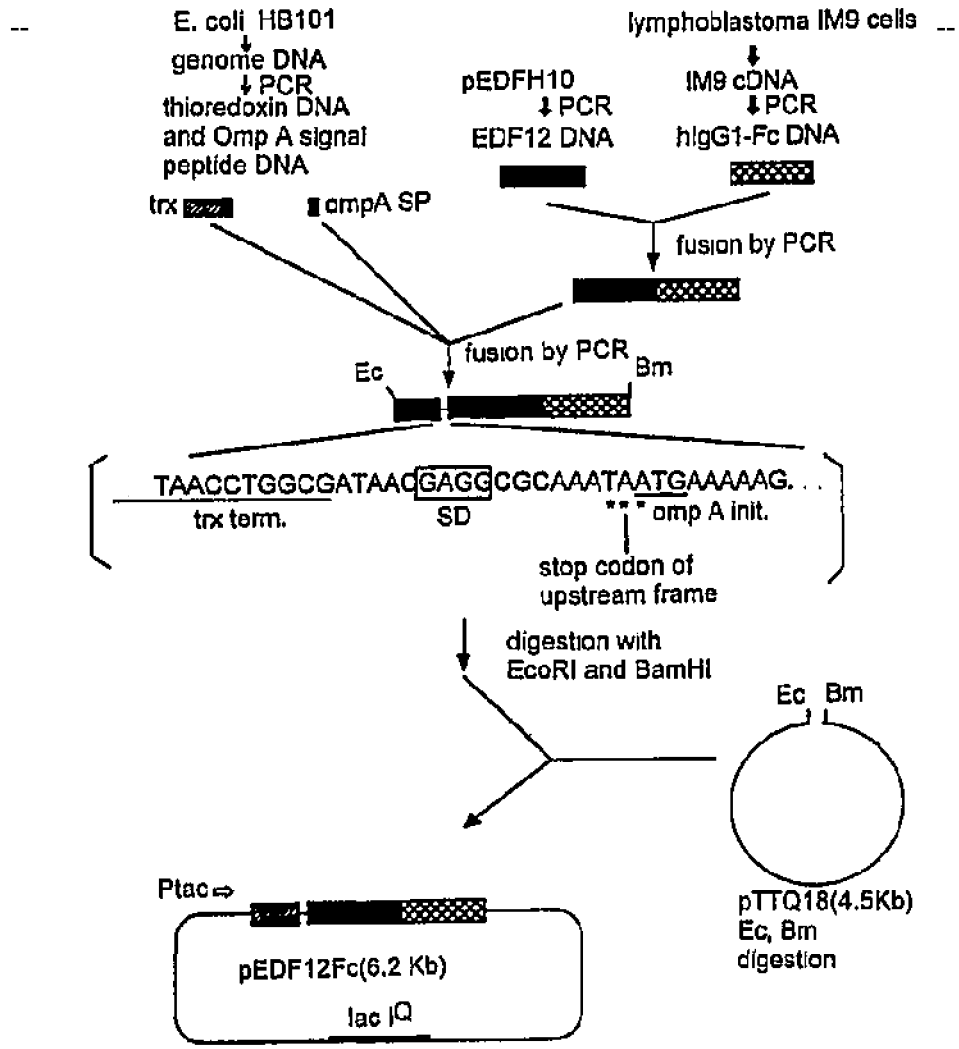

FIG. 14

UNITED STATES PATENT AND TRADEMARK OFFICE
CERTIFICATE OF CORRECTION

PATENT NO.       : 6,270,993 B1
APPLICATION NO.  : 09/051363
DATED            : August 7, 2001
INVENTOR(S)      : Masabumi Shibuya et al.

It is certified that error appears in the above-identified patent and that said Letters Patent is hereby corrected as shown below:

Drawings, Delete Fig. 18, and replace with Fig. 18, as shown below,

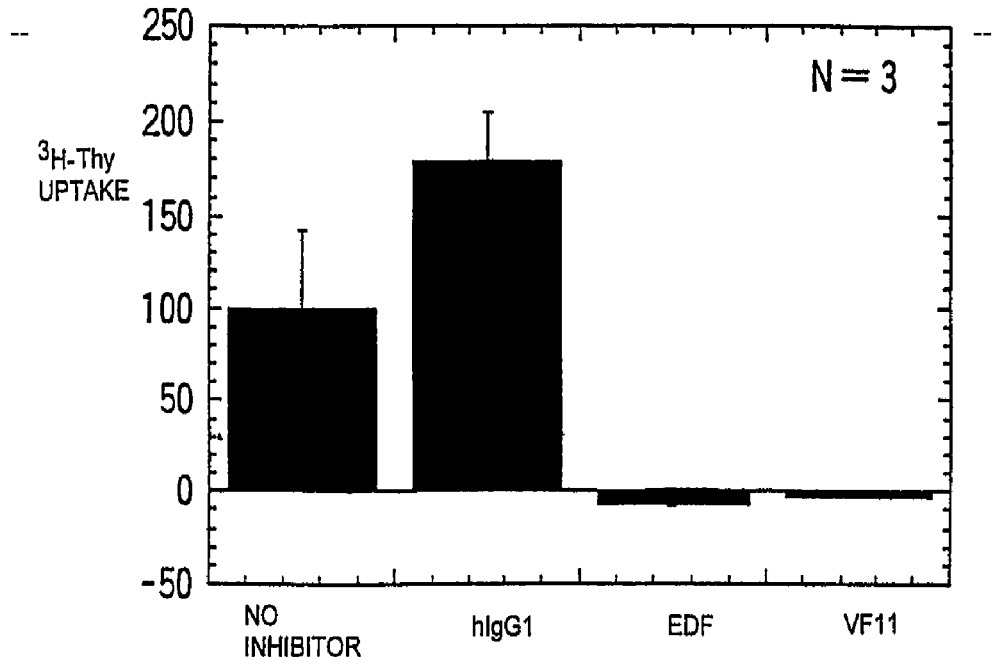

FIG. 18

Column 45,
Line 41, replace "call" with -- cell --

Signed and Sealed this

Twenty-fourth Day of July, 2007

JON W. DUDAS
*Director of the United States Patent and Trademark Office*